US008906888B2

(12) United States Patent
Saha et al.

(10) Patent No.: US 8,906,888 B2
(45) Date of Patent: Dec. 9, 2014

(54) LOW-CALCEMIC 16,23-DIENE 25-OXIME ANALOGS OF 1α,25-DIHYDROXY VITAMIN $D_3$

(75) Inventors: Uttam Saha, Thornhill (CA); Gary H. Posner, Baltimore, MD (US); Mehmet Kahraman, San Diego, CA (US)

(73) Assignees: Cytochroma Inc., Markham, Ontario (CA); Johns Hopkins University, Baltimore, MD (US)

( * ) Notice: Subject to any disclaimer, the term of this patent is extended or adjusted under 35 U.S.C. 154(b) by 1656 days.

(21) Appl. No.: 11/912,395

(22) PCT Filed: Apr. 25, 2006

(86) PCT No.: PCT/CA2006/000657
§ 371 (c)(1),
(2), (4) Date: Nov. 11, 2008

(87) PCT Pub. No.: WO2006/113990
PCT Pub. Date: Nov. 2, 2006

(65) Prior Publication Data
US 2009/0082317 A1 Mar. 26, 2009

Related U.S. Application Data

(60) Provisional application No. 60/674,282, filed on Apr. 25, 2005.

(51) Int. Cl.
*C07C 401/00* (2006.01)
*A61K 31/593* (2006.01)

(52) U.S. Cl.
CPC ................................. *C07C 401/00* (2013.01)
USPC .......................................... 514/167; 552/653

(58) Field of Classification Search
USPC .......................................... 514/167; 552/653
See application file for complete search history.

(56) References Cited

U.S. PATENT DOCUMENTS

| 6,982,258 B2 * | 1/2006 | Posner et al. ................. 514/167 |
| 2003/0171342 A1 | 9/2003 | Posner et al. |

FOREIGN PATENT DOCUMENTS

| CA | 2333270 | 12/1999 |
| WO | WO-03/031400 A1 | 4/2003 |
| WO | WO 03/093459 A1 | 11/2003 |

OTHER PUBLICATIONS

S.R. Vippagunta, et al. Advanced. Drug Delivery Rev. (2001) 48, pp. 1-26.*
Voskoglou-Nomikos et al., Clinica;l Cancer Research, vol. 9, pp. 4227-4239, Sep. 12, 2003.*
Adachi et al., "A novel Lyn-binding peptide inhibitor blocks eosinophil differentiation, survival, and airway eosinophilic inflammation," *J. Immunol.*, 163:939-946 (1999).
Armbrecht et al., "Characterization and regulation of the vitamin D hydroxylases," *J. Steroid Biochem. Molec. Biol.*, 43:1073-1081 (1992).
Beckman et al., "Assay of 25-hydroxyvitamin D 1 alpha-hydroxylase and 24-hydroxylase," *Methods Enzymol.*, 282:200-213 (1997).
Bell, "Renal and nonrenal 25-hydroxyvitamin D-1alpha-hydroxylases and their clinical significance," *J. Bone Miner. Res.*, 13:350-353 (1998).
Bouillon et al., "Comparative study of the affinity of the serum vitamin D-binding protein," *J. Steroid Biochem.*, 13:1029-1034 (1980).
Bouillon et al., "Structure-function relationships in the vitamin D endocrine system," *Endocr. Rev.*, 16:200-257 (1995).
Carlberg, "Molecular basis of the selective activity of vitamin D analogues," *J. Cell Biochem.*, 88:274-281 (2003).
Dilworth et al., "Construction of a P450c27 fusion enzyme: a useful tool for analysis of vitamin $D_3$ 25-hydroxylase activity," *Biochem. J.*, 320 (Pt. 1):267-271 (1996).
Enk et al., "T cell receptor mimic peptides and their potential application in T-cell-mediated disease," *Int. Arch. Allergy Immunol.*, 123:275-281 (2000).
Hawkes et al., "Nuclear magnetic resonance spectroscopy. Use of carbon-13 spectra to establish configurations of oximes," *J. Org. Chem.*, 39:1017-1028 (1974).
International Preliminary Report on Patentability for application No. PCT/CA2006/00657, dated Oct. 30, 2007.
International Search Report for application No. PCT/CA2006/00657, dated Dec. 12, 2006.
Jones et al., "Current understanding of the molecular actions of vitamin D," *Physiol. Rev.*, 78:1193-1231 (1998).
Jones et al., "Displacement potency of vitamin D2 analogs in competitive protein-binding assays for 25-hydroxyvitamin D3, 24,25-dihydroxyvitamin D3, and 1,25-dihydroxyvitamin D3," *J. Clin. Endocrinol. Metab.*, 50:773-775 (1980).
Kasyapa et al., "Regulation of IL-15-stimulated TNF-α production by rolipram," *J. Immunol.*, 163: 2836-2843 (1999).
Mathieu et al., "The coming of age of 1,25-dihydroxyvitamin D(3) analogs as immunomodulatory agents," *Trends Mol. Med.*, 8:174-179 (2002).
Nagpal et al., "Vitamin D analogs: mechanism of action and therapeutic applications," *Curr. Med. Chem.*, 8:1661-1679 (2001).
Pinette et al., "Vitamin D receptor as a drug discovery target," *Mini Rev. Med. Chem.*, 3:193-204 (2003).
Posner et al., "Antiproliferative hybrid analogs of the hormone 1alpha,25-dihydroxyvitamin D3: design, synthesis, and preliminary biological evaluation," *J. Org. Chem.*, 62:3299-3314 (1997).
Posner et al., "Conceptually new low-calcemic oxime analogues of the hormone 1alpha,25-dihydroxyvitamin D3: synthesis and biological testing," *J. Med. Chem.*, 45:1723-1730 (2002).

(Continued)

*Primary Examiner* — Sabiha N Qazi
(74) *Attorney, Agent, or Firm* — Marshall, Gerstein & Borun LLP

(57) ABSTRACT

The present invention provides novel 16,23-diene 25-oxime ether analogs of 1,25-dihydroxy vitamin D3, compositions comprising these compounds and methods of using these compounds as inhibitors of CYP24. In particular, the novel compound of the invention are useful for treating diseases which benefit from a modulation of the levels of 1,25-dihydroxy vitamin D3, for example, cell-proliferative disorders.

23 Claims, No Drawings

(56) References Cited

OTHER PUBLICATIONS

Posner et al., "New vitamin D3 derivatives with unexpected antiproliferative activity: 1-(hydroxymethyl)-25-hydroxyvitamin D3 homologs," *J. Med. Chem.*, 35:3280-3287 (1992).
Robinson et al., "Paricalcitol: a review of its use in the management of secondary hyperparathyroidism," *Drugs*, 65:559-576 (2005).
Ross et al., "Overproduction of rat 1,25-dihydroxyvitamin D3 receptor in insect cells using the baculovirus expression system," *Proc. Natl. Acad. Sci. USA*, 88:6555-6559 (1991).
Rückert et al., "Inhibition of keratinocyte apoptosis by IL-15: a new parameter in the pathogenesis of psoriasis?" *J. Immunol.*, 165:2240-2250 (2000).
Sawada et al., "Metabolism of vitamin D3 by human CYP27A1," *Biochem. Biophys. Res. Commun.*, 273:977-984 (2000).
Stein et al., "An update on the therapeutic potential of vitamin D analogues," *Expert Opin. Investig. Drugs*, 12:825-840 (2003).
Suffert, "Simple direct titration of organolithium reagents using N-pivaloyl-o-toluidine and/or N-pivaloyl-o-benzylaniline," *J. Org. Chem.*, 54:509-510 (1989).
Wecksler et al., "An hydroxylapatite batch assay for the quantitation of 1alpha,25-dihydroxyvitamin D3-receptor complexes," *Anal. Biochem.*, 92:314-323 (1979).
Beer et al. Am J Clin Oncol 27(5):535-541 (2004).
Beer et al., J Clin Oncol 21(1):123-128 (2003).
Bouillon et al., Endocrine Reviews 16(2):200-257 (1995).
Cheng and Coyne, Therapeutics and Clinical Risk Management 2(3):297-301 (2006).
Colston et al., British Journal of Cancer 76(8):1017-1020 (1997).
Fujioka et al., J Urol 160(1):247-251 (1998).
Huerta et al. Cancer Res 62:741-746 (2002).
Iseki et al., Int. J. Cancer 81:730-733 (1999).
Jones et al., Anticancer Research 26:2589-2596 (2006).
Kusudo et al. Biochemical and Biophysical Research Communications 309:885-892 (2003).
Kusudo et al., Biochemical and Biophysical Research Communications 321:774-782 (2004).
Masood et al., Blood 96(9):3188-3194 (2000).
Masuda et al., Biochimica et Biophysica Acta 1761:221-234 (2006).
Morris et al., Cancer 100(9):1868-1875 (2004).
Prudencio et al. Journal of the National Cancer Institute 93(10):745-753 (2001).
Rao et al. Cancer Research 64:2143-2147 (2004).
Sakaki et al., Biochemical Pharmacology 65:1957-1965 (2003).
Shankar et al., Archives of Biochemistry and Biophysics 387(2):297-306 (2001).
Trump et al. Cancer 106(10):2136-212 (2006).
Trydal et al., Cancer Res 48:2458-2461 (1988).
Zhou et al., Cancer Epidemiol Biomarkers Prev. 14(10):2303-2309 (2005).
Parise, Robert A., et al., "CYP24, the Enzyme that Catabolizes the Antiproliferative Agent Vitamin D, is Increased in Lung Cancer," *International Journal of Cancer*. 2006, vol. 119, pp. 1819-1828.
Chen et al., "An evaluation of 1,25-Dihydrroxyvitamin $D_3$ analogues on the proliferation and differentiation of cultured human keratinocytes, calcium metabolism and the differentiation of human HL-60 cells," *J. Nutr. Biochem.*, 4:49-57 (1993).
Supplemental European Search Report for counterpart EPO application No. EP06721850.3, dated Jul. 26, 2010.

* cited by examiner

LOW-CALCEMIC 16,23-DIENE 25-OXIME ANALOGS OF 1α,25-DIHYDROXY VITAMIN D$_3$

This invention was made with government support under NIH Grant Number CA 44530. The government has certain rights in the invention.

FIELD OF THE INVENTION

The present invention relates to novel analogs of the hormone 1α,25-dihydroxy vitamin D$_3$ that show selective inhibition of the enzyme CYP24 and which are low-calcemic and anti-proliferative, to pharmaceutical and diagnostic compositions containing them and to their medical use, particularly in the treatment and/or prevention of cancer, dermatological disorders, bone disorders, parathyroid disorders, immunological disorders, wound healing and osteoporosis.

BACKGROUND OF THE INVENTION

The vitamin D metabolic pathway is part of a vital endocrine system that is highly regulated at certain stages and produces metabolites that control the secretion of the parathyroid gland hormones (Beckman, M., and DeLuca, H. (1997) *Methods in Enzymol.* 282, 200-223; Jones, G., Strugnell, S., and DeLuca, H. (1998) *Physiol. Rev.* 78, 1193-1231). 1α,25-Dihydroxy vitamin D$_3$, also known as calcitriol (see below), a hormone produced in the vitamin D pathway, regulates phosphate and calcium levels in the blood which in turn control bone mass, the state of bones, and affects cellular differentiation in the skin and the immune system (Armbrecht, H. J., Okuda, K., Wongsurawat, N., Nemani, R., Chen, M., and Boltz, M. (1992) *J. Steroid Biochem. Molec. Biol.* 43, 1073-1081). In the vitamin D pathway, cytochrome P450s are enzymes that introduce functional groups by hydroxylation, usually at positions 1,25, and 24, of vitamin D$_3$ (Beckman, M., and DeLuca, H. (1997) *Methods in Enzymol.* 282, 200-223).

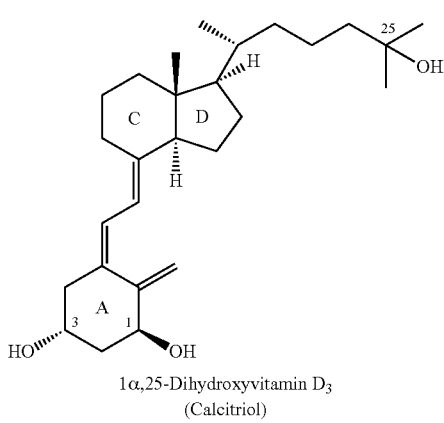

1α,25-Dihydroxyvitamin D$_3$
(Calcitriol)

1α,25-Dihydroxy vitamin D$_3$ is converted to 1α,24,25-trihydroxy-D$_3$ by a mitochondrial P450 known as CYP24 (Bell, N. H., (1998) *J. Bone Miner. Res.* 13, 350-35211). CYP24 is induced by 1α,25-dihydroxy-D$_3$ and is found in the kidney as well as other vitamin D target tissues such as the parathyroid cells, keratinocytes, osteoblasts, and enteroctyes (Jones, G., Strugnell, S., and DeLuca, H. (1998) *Physiol. Rev.* 78, 1193-1231). 1α,25-Dihydroxy vitamin D$_3$ (1,25-D3) has an important role in the antiproliferative and growth regulatory effects on normal and neoplastic cells (for e.g. prostate cancer cells). Clinical use of 1,25-D3 analogs as effective drugs requires antiproliferative and pro-differentiating activities.

Oxime ether analogs of 1α,25-dihydroxy vitamin D$_3$ having a fully saturated D-ring side chain are described in U.S. Pat. No. 6,982,258.

There is a continuing need for synthetic analogs of 1α,25-dihydroxy vitamin D$_3$ that selectively exhibit desirable pharmacological activities but do not exhibit hypercalcemic and other undesirable activities.

SUMMARY OF THE INVENTION

Novel 16,23-diene-25-oxime ether analogs of 1α,25-dihydroxy vitamin D$_3$ have been prepared that show selective inhibition of the enzyme CYP24, anti-proliferative activity and are low-calcemic.

The present invention therefore includes a compound selected from a compound of Formula I, and pharmaceutically acceptable salts, solvates, and prodrugs thereof:

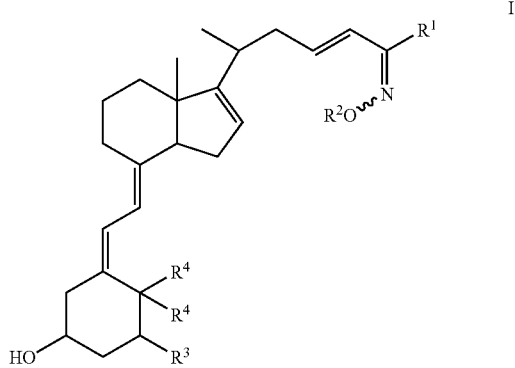

wherein
$R^1$ is selected from the group consisting of $C_{1-6}$alkyl, $C_{2-6}$alkenyl, cyclo($C_3$-$C_7$)alkyl and cyclo($C_3$-$C_7$)alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, $NH_2$, $NHC_{1-4}$ alkyl and $N(C_{1-4}$alkyl)($C_{1-4}$alkyl), and with cyclo($C_3$-$C_6$)alkyl and cyclo($C_3$-$C_6$)alkenyl being unsubstituted or substituted with 1-5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)O$C_{1-4}$alkyl, C(O)NH$C_{1-4}$alkyl, NHC(O)$C_{1-4}$alkyl, OC(O)$C_{1-4}$alkyl, SO$C_{1-4}$alkyl, $SO_2C_{1-4}$alkyl, $SO_2NHC_{1-4}$alkyl and $SO_2NH_2$;

$R^2$ is selected from the group consisting of H, $C_{1-6}$alkyl and $C_{2-6}$alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl);

$R^3$ is selected from the group consisting of OH, $OC_{1-6}$alkyl, and halo; and $R^4$ are either both H or together form $=CH_2$.

Suitably, the compounds of the invention have the stereochemistry of natural 1α,25-dihydroxy vitamin D$_3$. Therefore, in an embodiment, the present invention includes a compound selected from a compound of Formula I, and pharmaceutically acceptable salts, solvates, and prodrugs thereof, as shown below:

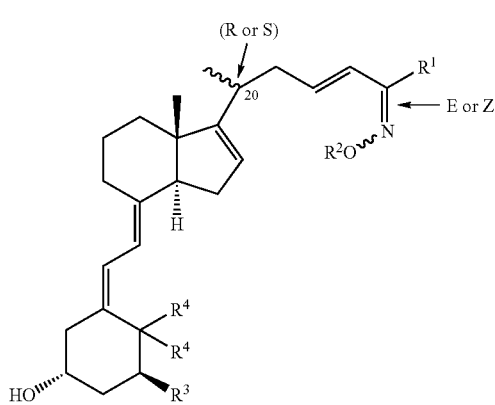

wherein
R¹-R⁴ are as defined above. In an embodiment, the compounds of the invention possess the E stereochemistry at the oxime double bond.

According to another aspect of the present invention, there is included a pharmaceutical composition comprising a compound of the invention and a pharmaceutically acceptable carrier or diluent.

By selectively modulating CYP24, the enzyme that metabolizes 1α,25-dihydroxy vitamin $D_3$, the levels of 1α,25-dihydroxy vitamin $D_3$ are also modulated. Diseases that benefit from a modulation of the levels of 1α,25-dihydroxy vitamin $D_3$ can therefore be treated using a modulator of CYP24. By acting preferentially on CYP24, side effects caused by interaction with other enzymes and receptors will be reduced. Accordingly, the present invention provides a method for treating a disease which benefits from a modulation of levels of 1α,25-dihydroxy vitamin $D_3$ comprising administering an effective amount of a compound of the invention to a cell or animal in need thereof. The invention also includes the use of a compound of the invention to treat a disease which benefits from a modulation of levels of 1α,25-dihydroxy vitamin $D_3$. Further, the invention includes a use of a compound of the invention to prepare a medicament to treat a disease which benefits from a modulation of levels of 1α,25-dihydroxy vitamin $D_3$.

Inhibition of CYP24 inhibits the catabolism of 1α,25-dihydroxy vitamin $D_3$ which will lengthen the biological lifetime of this hormone and thus allow smaller amounts of it to be used for effective disease treatment. Such smaller dosing will avoid, or at least minimize, the hypercalcemic toxicity associated with medicinal use of 1α,25-dihydroxy vitamin $D_3$ (calcitriol). Therefore, in a further embodiment, the present invention includes a method for treating a disease which benefits from inhibiting catabolism of 1α,25-dihydroxy vitamin $D_3$ comprising administering an effective amount of a compound of the invention to a cell or animal in need thereof. The invention also includes the use of a compound of the invention to treat a disease which benefits from an inhibition of catabolism of 1α,25-dihydroxy vitamin $D_3$. Further, the invention includes a use of a compound of the invention to prepare a medicament to treat a disease which benefits from an inhibition of catabolism of 1α,25-dihydroxy vitamin $D_3$.

Diseases which may benefit from a modulation in levels of 1α,25-dihydroxy vitamin $D_3$ include, but are not limited to:
(i) in the parathyroid—hyper- and hypo-parathyroidism, pseudohypo-parathyroidism and secondary hyperparathyroidism;
(ii) in the pancreas—diabetes;
(iii) in the thyroid—medullary carcinoma;
(iv) in the skin—psoriasis and wound healing;
(v) in the lung—sarcoidosis and tuberculosis;
(vi) in the kidney—chronic renal disease, hypophosphatemic vitamin D dependent rickets and vitamin D dependent rickets;
(vii) in the bone—anticonvulsant treatment, fibrogenisis imperfecta ossium, osteitits fibrosa cystica, osteomalacia, osteoporosis, osteopenia, osteosclerosis, renal osteodytrophy and rickets;
(viii) in the intestine—glucocorticoid antagonism, idopathic hypercalcemia, malabsorption syndrome, steatorrhea and tropical sprue.

The compounds of Formula I, or salts, solvates or prodrugs thereof, can be used alone or in combination with other agents that modulate CYP24 activity or in combination with other types of treatment (which may or may not modulate CYP24) for cell proliferative disorders or other disorders that benefit from a modulation in the levels of 1α,25-dihydroxy vitamin $D_3$ and/or an inhibition of the catabolism of 1α,25-dihydroxy vitamin $D_3$. Suitably the compounds of Formula I are administered in combination with 1α,25-dihydroxy vitamin $D_3$ (calcitriol) or another vitamin D receptor agonist. The present invention therefore includes a method of increasing the efficacy of a vitamin D receptor agonist, suitably 1α,25-dihydroxy vitamin $D_3$ (calcitriol), comprising contemporaneously administering an effective amount of a compound of the invention and an effective amount of the vitamin D receptor agonist, suitably 1α,25-dihydroxy vitamin $D_3$ (calcitriol). Further the invention includes a use of a compound of the invention to increase the efficacy of a vitamin D receptor agonist, suitably 1α,25-dihydroxy vitamin $D_3$ (calcitriol), and a use of a compound of the invention to prepare a medicament to increase the efficacy of a vitamin D receptor agonist, suitably 1α,25-dihydroxy vitamin $D_3$ (calcitriol).

In accordance with a further aspect of the present invention, there is included a method for treating a cell proliferative disorder comprising administering an effective amount of a compound of the invention to a cell or animal in need thereof. The invention also includes a use of a compound of the invention to treat a cell proliferative disorder. The invention further includes a use of a compound of the invention to prepare a medicament to treat a cell proliferative disorder, suitably to inhibit cell proliferation.

In an embodiment, the present invention also includes a method of inhibiting the proliferation of a cancer cell comprising administering an effective amount of a compound of the invention to a cell or animal in need thereof. The invention also includes a use of a compound of the invention to inhibit cancer cell proliferation. The invention further includes a use of a compound of the invention to prepare a medicament to inhibit cancer cell proliferation.

It is to be appreciated that the inhibition of cell proliferation by the compounds of the invention may be effected by mechanisms other than CYP24 inhibition.

In a further aspect, the invention includes a method of treating a disease which benefits from modulating CYP24 activity, suitably inhibiting CYP24 activity, comprising administering an effective amount of a compound of the invention to a cell or animal in need thereof. The present invention also includes a use of a compound of the invention to treat a disease which benefits from a modulation, suitably an inhibition, of CYP24 activity. The present invention further includes a use of a compound of the invention to prepare a medicament to treat a disease which benefits from a modulation, suitably an inhibition, of CYP24 activity.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

I. Definitions

The term "$C_{1-n}$alkyl" as used herein means straight and/or branched chain, saturated alkyl groups containing from one to n carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "$C_{2-n}$alkenyl" as used herein means straight and/or branched chain, unsaturated alkyl groups containing from two to n carbon atoms and one or two double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "cyclo($C_3$-$C_n$)alkyl" as used herein means saturated cyclic alkyl groups containing from three to n carbon atoms and includes (depending on the identity of n) cyclopropyl, cyclopentyl, cyclohexyl and cycloheptyl.

The term "cyclo($C_3$-$C_7$)alkenyl" as used herein means unsaturated, non-aromatic cyclic alkenyl groups containing from three to six carbon atoms and one double bond includes cyclopropenyl, cyclopentenyl, cyclohexenyl.

The term "halo" as used herein means halogen and includes chloro, fluoro, bromo and iodo.

The term "solvate" as used herein means a compound of the invention, or a salt of a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formula I, and salts, solvates and prodrugs thereof.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound of the invention, or any of its intermediates. Basic compounds of the invention that may form an acid addition salt include, for example, where the $C_{1-6}$alkyl group of $R^1$ and/or $R^2$ is substituted with a group having a basic nitrogen, for example $NH_2$ and $NHC_{1-4}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include, for example, where the $C_{1-6}$alkyl group of $R^1$ and/or $R^2$ is substituted with a group having acidic hydrogen, for example C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that modulates CYP24 activity, an effective amount of an agent is, for example, an amount sufficient to achieve such a modulation in CYP24 activity as compared to the response obtained without administration of the agent.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Design of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as CYP24 activity) as well as the enhancement of a function or activity.

To "inhibit" or "suppress" or "reduce" a function or activity, such as CYP24 activity, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The term "cancer cells" as used herein includes all forms of cancer or neoplastic disease.

The term "catabolism" as used herein refers to the metabolic process by which organisms convert substances into compounds for excretion.

The term "1α,3β-stereochemistry" as used herein refers to the relative configuration of the OH group at C-3, and $R^3$ in which $R^3$ is above the plane of the page, and the OH group at C-3 is below the plane of the page.

II. Compounds of the Invention

Novel compounds showing selective inhibition of the enzyme CYP24, antiproliferative activity and that are low-calcemic have been prepared. As such, the compounds of the invention are useful for treating cell proliferative diseases, such as cancer.

Accordingly, the present invention provides a compound selected from a compound of Formula I, and pharmaceutically acceptable salts, solvates, and prodrugs thereof:

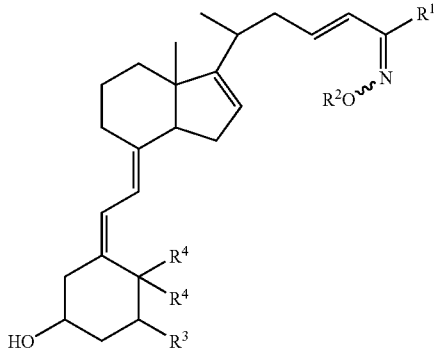

I wherein
$R^1$ is selected from the group consisting of $C_{1-6}$alkyl, $C_{2-6}$alkenyl, cyclo($C_3$-$C_7$)alkyl and cyclo($C_3$-$C_7$)alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, $NH_2$, $NHC_{1-4}$alkyl and $N(C_{1-4}$alkyl)($C_{1-4}$alkyl), and with cyclo($C_3$-$C_6$)alkyl and cyclo($C_3$-$C_7$)alkenyl being unsubstituted or substituted with 1-5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)$OC_{1-4}$alkyl, C(O)$NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;

$R^2$ is selected from the group consisting of H, $C_{1-6}$alkyl and $C_{2-6}$alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl);

$R^3$ is selected from the group consisting of OH, $OC_{1-6}$alkyl, and halo; and $R^4$ are either both H or together form $=CH_2$.

The present invention includes compounds of Formula I wherein $R^1$ is selected from the group consisting of $C_{1-6}$alkyl, $C_{2-6}$alkenyl, cyclo($C_3$-$C_7$)alkyl and cyclo($C_3$-$C_7$)alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, $NH_2$, $NHC_{1-4}$alkyl and $N(C_{1-4}$alkyl)($C_{1-4}$alkyl), and with cyclo($C_3$-$C_6$)alkyl and cyclo($C_3$-$C_6$)alkenyl being unsubstituted or substituted with 1-5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)$OC_{1-4}$alkyl, C(O)$NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In embodiments of the invention, $R^1$ is $C_{1-4}$alkyl or $C_{3-6}$cycloalkyl with $C_{1-4}$alkyl being unsubstituted or substituted with one or more halo groups or substituted with 1-2 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl) and with cyclo($C_3$-$C_6$)alkyl being unsubstituted or substituted with 1-2 groups independently selected from $C_{1-4}$alkyl, $OC_{1-4}$alkyl, OH, $CF_3$, $OCF_3$, halo, $NH_2$, $NHC_{1-4}$alkyl, and $N(C_{1-4}$alkyl)($C_{1-4}$alkyl). In further embodiments, $R^1$ is $C_{1-4}$alkyl or $C_{3-5}$cycloalkyl with $C_{1-4}$alkyl being unsubstituted or substituted with one or more halo groups or substituted with 1-2 groups independently selected from $C_{1-2}$alkyl, $OC_{1-2}$alkyl, OH, halo, $NH_2$, $NHC_{1-2}$alkyl and $N(C_{1-2}$alkyl)($C_{1-2}$alkyl) and with cyclo($C_3$-$C_5$)alkyl being unsubstituted or substituted with 1-2 groups independently selected from $C_{1-2}$alkyl, $OC_{1-2}$alkyl, OH, $CF_3$, $OCF_3$, halo, $NH_2$, $NHC_{1-2}$alkyl, and $N(C_{1-2}$alkyl)($C_{1-2}$alkyl). In further embodiments, $R^1$ is $C_{1-4}$alkyl or $C_{3-5}$cycloalkyl with $C_{1-4}$alkyl being unsubstituted or substituted with one or more halo groups or substituted with 1 group selected from $CH_3$, $OCH_3$, OH, halo, $NH_2$, $NHCH_3$ and $N(CH_3)_2$ and with cyclo($C_3$-$C_5$)alkyl being unsubstituted or substituted with 1 group selected from $CH_3$, $OCH_3$, OH, halo, $NH_2$, $NHCH_3$ and $N(CH_3)_2$. In still further embodiments, $R^1$ is selected from t-butyl, cyclopropyl, $CF_3$ and $C(CF_3)_3$.

The present invention includes compounds of Formula I wherein $R^2$ is selected from the group consisting of H, $C_{1-6}$alkyl and $C_{2-6}$alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl). In embodiments of the invention, $R^2$ is selected from the group consisting of H and $C_{1-4}$alkyl with $C_{1-4}$alkyl being unsubstituted or substituted with 1-2 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl). In further embodiments, $R^2$ is selected from the group consisting of H and $C_{1-4}$alkyl. In still further embodiments, $R^2$ is selected from the group consisting of H, $CH_3$, ethyl and allyl.

The compounds of Formula I include those in which $R^3$ is selected from the group consisting of OH, $OC_{1-6}$alkyl, and halo. In embodiments of the invention, $R^3$ is selected from the group consisting of OH, $OCH_3$, and fluoro. In a further embodiment, $R^3$ is OH.

The present invention also includes compounds of Formula I, wherein $R^4$ are either both H or together form $=CH_2$. In embodiments of the invention, $R^4$ is $=CH_2$.

All of the compounds of Formula I have more than one asymmetric centre. Where the compounds according to the invention possess more than one asymmetric centre, they may exist as diastereomers. It is to be understood that all such isomers and mixtures thereof in any proportion are encompassed within the scope of the present invention. Further, the invention extends to all geometric isomers of the present invention. For example, where there is a double bond in a compound of the invention, there may exist geometric isomers, such as cis and trans (also known as Z and E) isomers. In particular, the compounds of the invention may exist as geometric isomers at the oxime double bond. The invention includes both the E- and Z-oximes, including mixtures thereof. The stereochemistry of the compounds of the invention is suitably that of natural $1\alpha,25$-dihydroxy vitamin $D_3$. Therefore, in a suitable embodiment, the present invention provides compounds of Formula I with the relative stereochemistry as shown below, and pharmaceutically acceptable salts, hydrates and prodrugs thereof:

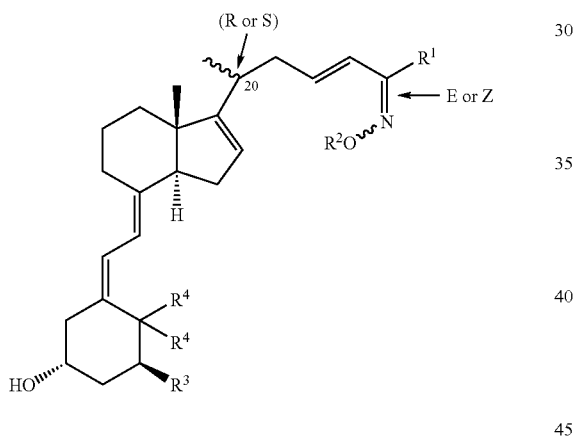

wherein $R^1$-$R^4$ are as defined above for Formula I. Suitably the stereochemistry at C-20 is R. Suitably the stereochemistry at the oxime double bond is predominantly E. It is to be understood that while, the relative stereochemistry of the compounds of Formula I is suitably as shown above, such compounds of Formula I may also contain certain amounts (e.g. less than 20%, preferably less than 10%, more preferably less than 5%) of compounds of Formula I having alternate stereochemistry. For example, a compound of Formula I having the $1\alpha,3\beta$-stereochemistry of natural $1\alpha,25$-dihydroxy Vitamin $D_3$, shown above, may contain less than 20%, suitably less than 10%, more suitably less than 5%, of a compound of Formula I having the unnatural $1\beta,3\alpha$-stereochemistry. Further, a compound of Formula I having the E stereochemistry at the oxime double bond, may contain less than 30%, suitably less than 20%, more suitably less than 10% of a compound of Formula I having the Z stereochemistry at the oxime double bond.

In specific embodiments of the present invention, the compounds of Formula I is selected from:

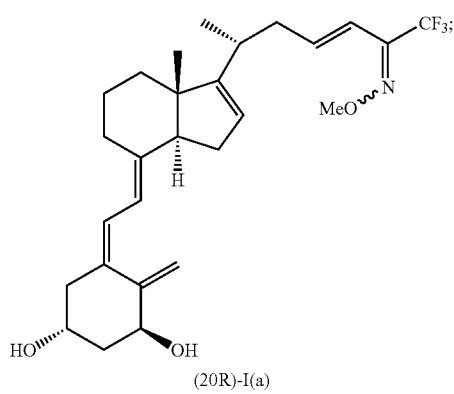
(20R)-I(a)

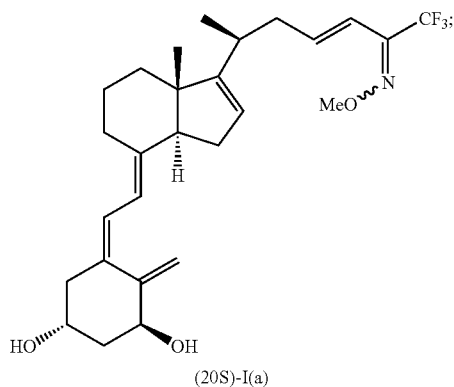
(20S)-I(a)

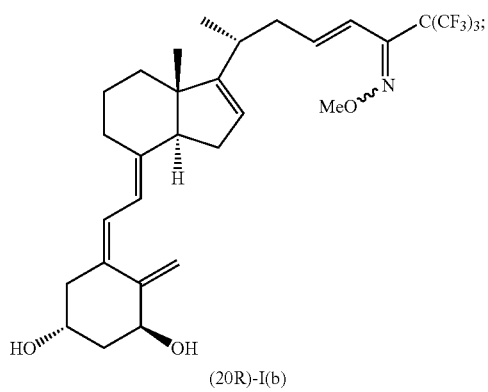
(20R)-I(b)

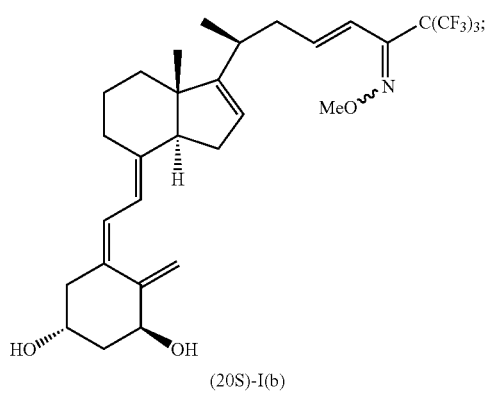
(20S)-I(b)

-continued
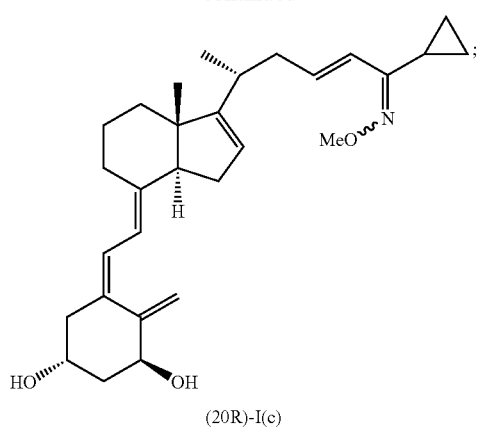
(20R)-I(c)
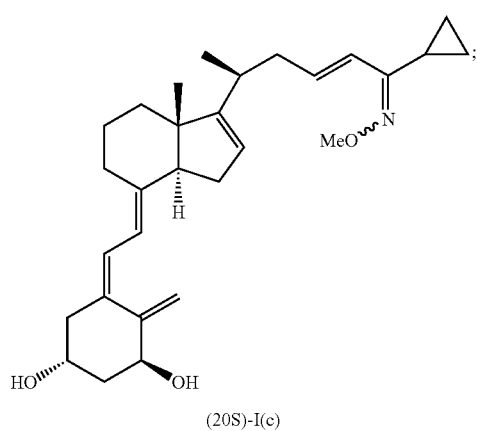
(20S)-I(c)
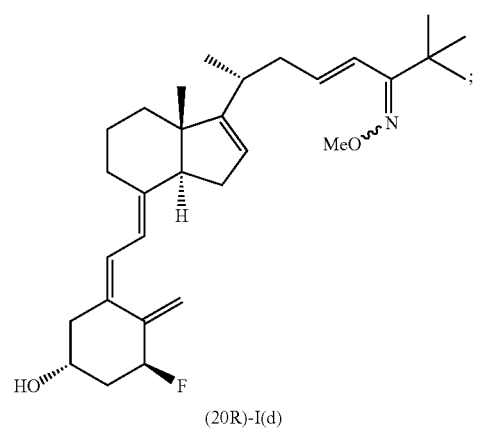
(20R)-I(d)
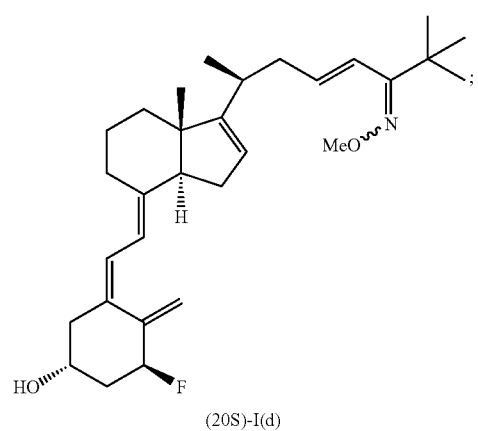
(20S)-I(d)
-continued
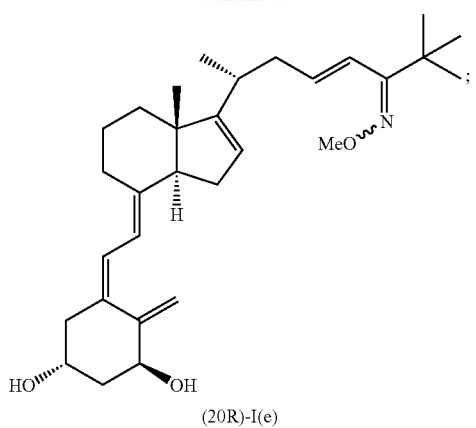
(20R)-I(e)
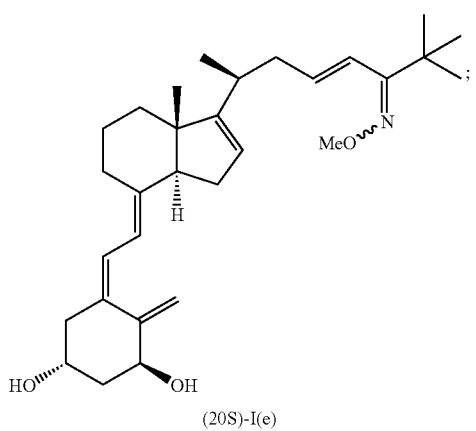
(20S)-I(e)
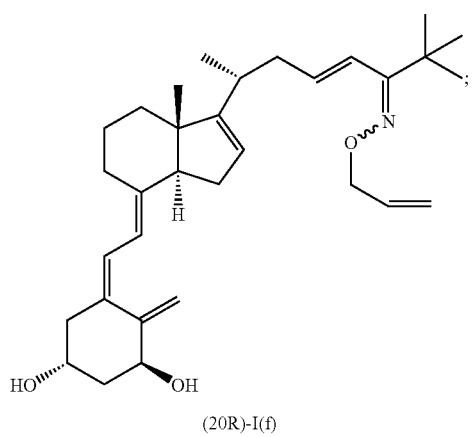
(20R)-I(f)
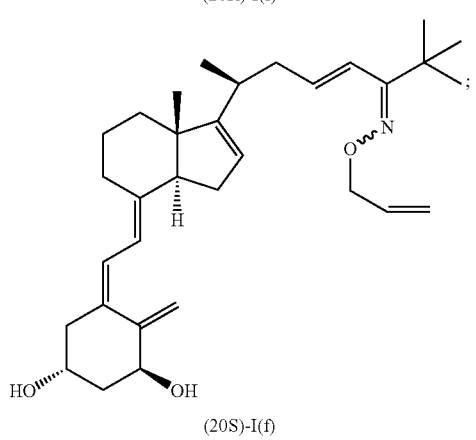
(20S)-I(f)

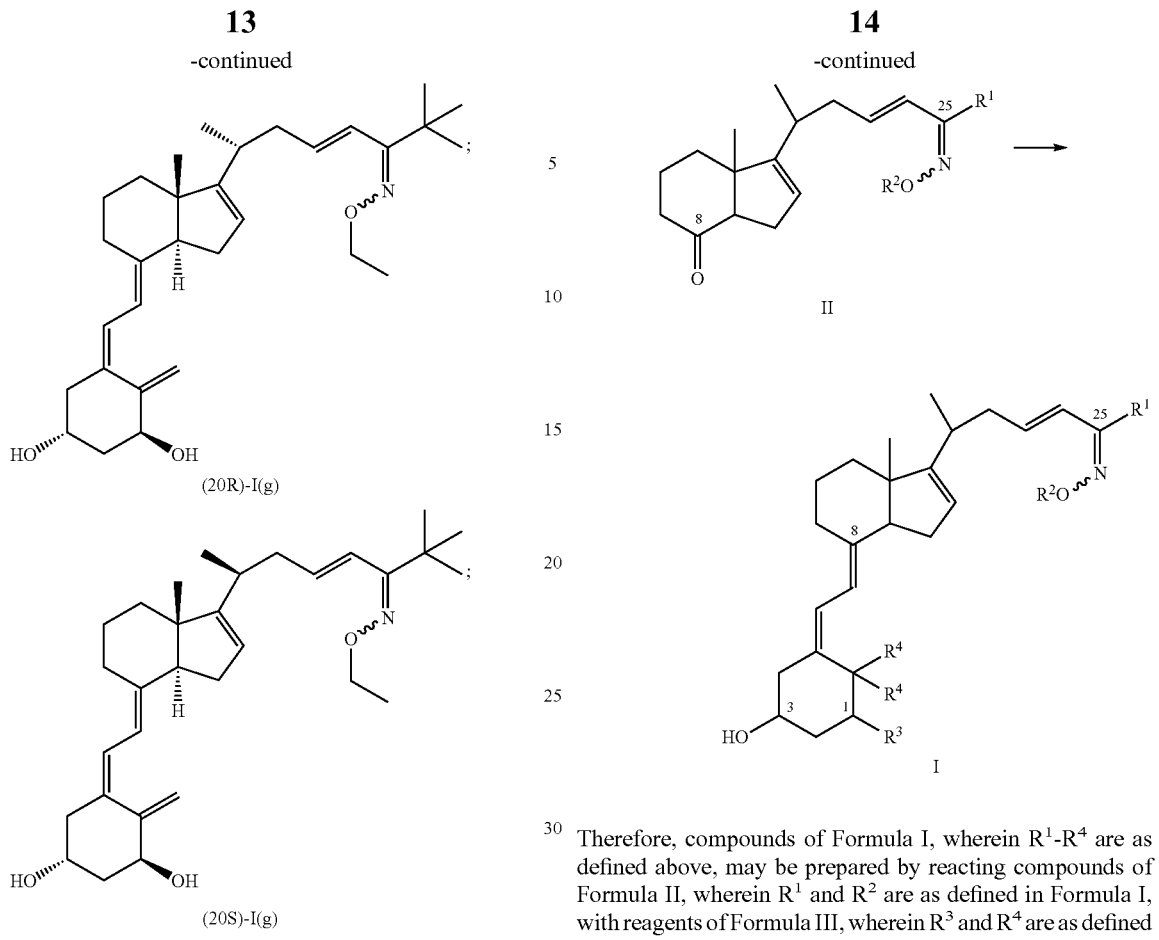

(20R)-I(g)

(20S)-I(g)

and pharmaceutically acceptable salts, solvates and prodrugs thereof. In an embodiment, the compounds of the invention possess the E stereochemistry at the oxime double bond. In a further embodiment of the invention, the compound of the invention is (20R)-I(a) or (20S)-I(a), (20R)-I(c) or (20S)-I(c), (20R)-I(e) or (20S)-I(e), suitably (20R)-I(a), (20R)-I(c) or 20(R)-I(e), as shown above, and pharmaceutically acceptable salts, solvates and prodrugs thereof.

III. Methods of Preparing Compounds of the Invention

In accordance with another aspect of the present invention, the compounds of the invention can be prepared by processes analogous to those established in the art. Therefore, compounds of this invention may be prepared, for example, by the reaction sequence shown in Scheme 1:

Scheme 1

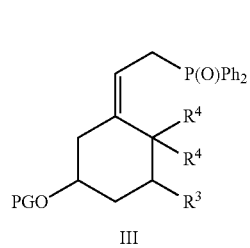

III

Therefore, compounds of Formula I, wherein $R^1$-$R^4$ are as defined above, may be prepared by reacting compounds of Formula II, wherein $R^1$ and $R^2$ are as defined in Formula I, with reagents of Formula III, wherein $R^3$ and $R^4$ are as defined in Formula I, under standard Horner-Wadsworth-Emmons (HWE) coupling conditions (see Posner, G. H. et al. *J. Org Chem.*, 1997, 62, 3299-3314). Therefore phosphine oxides III are treated with a strong base, for example an alkyl lithium such as n-butyllithium, under anhydrous conditions in an inert atmosphere and solvent, for example tetrahydrofuran (THF), at temperatures in the range of about –60° C. to about –90° C., suitably at about –78° C. To the resulting intermediate ylide is added a cold, suitably at about –78° C., solution of a ketone II in an inert solvent such as THF while maintaining the anhydrous conditions. After removal of any protecting groups using standard chemistries (if needed), compounds of Formula I may be obtained.

Ketones of Formula II, wherein $R^1$ and $R^2$ are as defined in Formula I, may be prepared, for example, as shown in Scheme 2:

Scheme 2

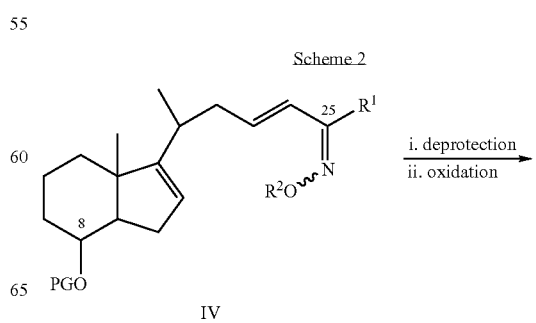

IV

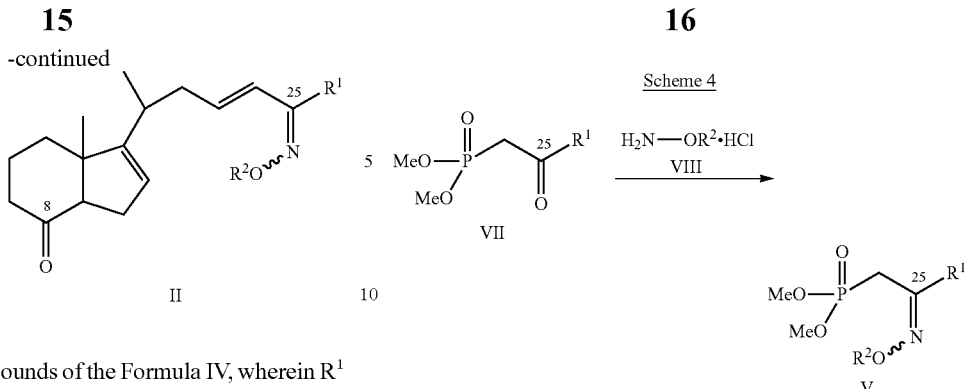

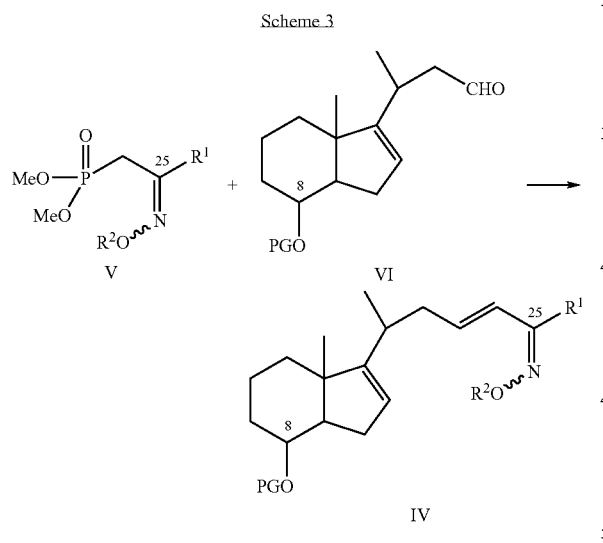

Suitably protected compounds of the Formula IV, wherein $R^1$ and $R^2$ are as defined in Formula I and PG is a suitable protecting group, are first deprotected and then oxidized to provide ketones II. For example, when PG is trialkyl silyl, such as tributyl silyl, deprotection may be affected by reacting compounds of Formula IV with tetrabutylammonium fluoride (TBAF) in an inert solvent, such as THF, and in an inert atmosphere, suitably at about room temperature. Oxidation of the resulting alcohol may be performed, for example, using pyridinium dichromate (PDC), or any other suitable oxidizing agent, in an inert solvent such as methylene chloride, under standard conditions.

Compounds of the Formula IV, wherein $R^1$ and $R^2$ are as defined in Formula I and PG is a suitable protecting group, may be prepared, for example, as shown in Scheme 3:

Phosphonates of Formula V, wherein $R^1$ and $R^2$ are as defined in Formula I, may be used to prepare olefins of Formula IV, when reacted with aldehydes of Formula VI, wherein PG is a suitable protecting group, in the presence of a strong base. Therefore phosphonates V are treated with a strong base, for example a potassium alkoxide such as potassium t-butoxide, under anhydrous conditions in an inert atmosphere and solvent, for example THF, at a temperature of about 0° C. To the resulting carbanion is added a cold, suitably at about 0° C., solution of aldehyde VI in an inert solvent such as THF while maintaining the anhydrous conditions. Compounds of Formula IV may be obtained accordingly.

Compounds of Formula V, wherein $R^1$ and $R^2$ are as defined in Formula I, may be prepared, for example, as in Scheme 4:

Therefore, compounds of Formula V, wherein $R^1$ and $R^2$ are as defined in Formula I may be prepared by reacting compounds of Formula VIII or a salt or hydrate thereof, wherein $R^2$ is as defined in Formula I, with reagents of Formula VII, wherein $R^1$ is as defined in Formula I, suitably in the presence of a non-nucleophilic amine, at temperatures in the range of 0° C. to about 40° C., suitably at room temperature. The non-nucleophilic amine may be any tertiary aromatic or aliphatic amine, for example pyridine, and is suitably present in excess amounts. When pyridine is the non-nucleophilic amine, it is suitably also used as a solvent for the transformation of compounds VII to V. The E-oxime alkyl ether of the Formula V is predominantly obtained due to the strongly unfavourable steric congestion that would be present in the corresponding Z-oxime alkyl ether (see Hawkes, G. E. and Herwig, K.; Roberts, J. D. *J. Org. Chem.* 1974, 39, 1017-1028). The E- and Z-oximes may be separated using standard chromatographic techniques.

Compounds of the Formula VII, wherein $R^1$ is as defined in Formula I, may be prepared, for example, as in Scheme 5:

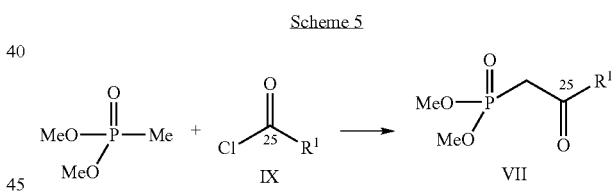

Accordingly, compounds of Formula VII, wherein $R^1$ is as defined in Formula I, may be prepared by reacting acyl chlorides of Formula IX with dimethyl-methylphosphonate in the presence of a strong base. Therefore, dimethyl-methylphosphonate is treated with a strong base, for example an alkyl lithium such as butyl lithium, under anhydrous conditions in an inert atmosphere and solvent, for example THF, in the range of about −60° C. to about −90° C., suitably at about −78° C. To the resulting intermediate carbanion is added to a cold, suitably at about −78° C., solution of a acyl chloride VIII in an inert solvent such as THF while maintaining the anhydrous conditions. Compounds of Formula VII are thus obtained. Compounds of the Formula VIII and IX are either commercially available or are readily prepared using methods known in the art. The preparation of compounds of Formula III, wherein $R^3$ and $R^4$ are as defined in Formula I is known in the art. Therefore compounds of Formula III may be prepared as described in Posner, G. H. et al. *J. Med. Chem.* 1992, 35, 3280-3287, the contents of which are incorporated herein by reference.

The preparation of enantiomerically pure compounds of Formula I may be accomplished by using enantiomerically pure compounds of Formulae III and VI in the reactions shown in Schemes 1 and 3, respectively. In the reaction in Scheme 1, a mixture of the 1α,3β and 1β, 3α diasteromers is typically obtained, with the 1α,3β diastereomer as the major product. These diasteromers may be separated using chromatography, for example using high performance liquid chromatography (HPLC).

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, $3^{rd}$ Edition, 1999.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of Formula I may be, for example, conventional esters formed with available hydroxy, thiol, amino or carboxyl group. For example, the OH at C-3 and/or the OH at $R^3$ may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters.

The present invention includes radiolabeled forms of the compounds of the invention, for example, compounds of the invention labeled by incorporation within the structure $^3H$, $^{11}C$ or $^{14}C$ or a radioactive halogen such as $^{125}I$ and $^{18}F$. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}F$]/K222 with a suitable precursor compound, such as a compound of Formula I comprising a suitable leaving group, for example a tosyl group, that may be displaced with the $^{18}F$ anion.

IV. Uses

As hereinbefore mentioned, novel compounds of the Formula I have been prepared. Accordingly, the present invention includes all uses of the compounds of the invention including their use in therapeutic methods and compositions for modulating cell proliferation, their use in diagnostic assays and their use as research tools and as starting materials and/or intermediates in the preparation of other chemical entities.

Inhibiting catabolism of calcitriol will lengthen the biological lifetime of this hormone and thus allow smaller amounts of it to be used for effective human chemotherapy; such smaller dosing will avoid, or at least minimize, the hypercalcemic toxicity associated with medicinal use of calcitriol. Selectively inhibiting the cytochrome P450 enzymatic pathway, through which calcitriol is catabolized (mainly via C-24 hydroxylation), is one important way to prolong the lifetime of this hormone. Therefore, the compounds of Formula I were tested in vitro, using a standard protocol, for their ability to specifically inhibit CYP24, responsible for 24-hydroxylation of calcitriol. Antimycotic ketoconazole, a drug used clinically for chemotherapy of human prostate cancer (Trachtenberg, J. et al. J. Urol. 1984, J32, 61-63), was used as a control standard for inhibition of CYP24. Selected compounds of Formula I were more potent than ketoconazole in inhibiting CYP24 activity. These compounds showed little to no inhibition of the enzymes CYP27A1 and CYP27B1, indicating that they can selectively inhibit CYP24 activity. Selected compounds of Formula I were also shown to induce CYP24 mRNA expression.

Selected compounds of Formula I have also been shown to have in vitro antiproliferative activity in breast cancer (MCF-7), ovarian cancer (OVCAR-3), head and neck cancer (SCC-25), prostate cancer (LNCaP) and pancreatic cancer (BxPC-3) cell lines. Also, in standard hypercalcemia assays, selected compounds of Formula I did not increase the levels of calcium in the urine of a rat after they were administered orally to the rats daily for one week. At similar doses, calcitriol causes a significant increase in calcium levels in the urine.

The compounds of Formula I are CYP24 modulators and are useful in modulating CYP24 activity, including the inhibition of CYP24 activity, for the treatment of various conditions such as cell proliferative disorders. Accordingly, the present invention includes a method of treating a disease which benefits from a modulation of CYP24 activity comprising administering an effective amount of a compound of the invention to a cell or animal in need thereof. In a further aspect, the invention includes a method of treating a disease which benefits from an inhibition of CYP24 activity comprising administering an effective amount of a compound of the invention to a cell or animal in need thereof. The present invention also includes the use of a compound of the invention to treat a disease which benefits from a modulation of, suitably an inhibition of, CYP24 activity and a use of a compound of the invention to prepare a medicament to treat a disease which benefits from a modulation of, suitably an inhibition of, CYP24 activity.

By selectively inhibiting CYP24, the enzyme that metabolizes 1α,25-dihydroxy vitamin $D_3$, the levels of 1α,25-dihydroxy vitamin $D_3$ will be increased. Diseases that benefit from an increase of the levels of 1α,25-dihydroxy vitamin $D_3$ can therefore be treated using a modulator of CYP24. By acting preferentially on CYP24, side effects caused by interaction with other enzymes and receptors will be reduced. Accordingly, the present invention includes a method of treating a disease which benefits from an increase of the levels of 1α,25-dihydroxy vitamin $D_3$ comprising administering an effective amount of a compound of the invention to a cell or animal in need thereof. The invention also includes the use of a compound of the invention to treat a disease which benefits from an increase of the levels of 1α,25-dihydroxy vitamin $D_3$.

Further, the invention includes a use of a compound of Formula I to prepare a medicament to treat a disease which benefits from an increase of the levels of 1α,25-dihydroxy vitamin $D_3$.

Inhibition of CYP24, will inhibit the catabolism 1α,25-dihydroxy vitamin $D_3$ which will lengthen the biological lifetime of this hormone and allow smaller amounts of it to be used for effective disease treatment. Such smaller dosing will avoid, or at least minimize, the hypercalcemic toxicity associated with medicinal use of 1α,25-dihydroxy vitamin $D_3$ (calcitriol). Therefore, in an embodiment, the present invention includes a method for treating a disease which benefits from inhibiting the catabolism of 1α,25-dihydroxy vitamin $D_3$ comprising administering an effective amount of a compound of the invention to a cell or animal in need thereof. The invention also includes the use of a compound of the invention to treat a disease which benefits from an inhibition of the catabolism of 1α,25-dihydroxy vitamin $D_3$. Further, the invention includes a use of a compound of Formula I to prepare a medicament to treat a disease which benefits from an inhibition of the catabolism of 1α,25-dihydroxy vitamin $D_3$.

Diseases which may benefit for a modulation (inhibition) in the levels of 1α,25-dihydroxy vitamin $D_3$ include, but are not limited to:
  (i) in the parathyroid—hyper- and hypo-parathyroidism, pseudohypo-parathyroidism and secondary hyperparathyroidism;
  (ii) in the pancreas—diabetes;
  (iii) in the thyroid—medullary carcinoma;
  (iv) in the skin—psoriasis and wound healing;
  (v) in the lung—sarcoidosis and tuberculosis;
  (vi) in the kidney—chronic renal disease, hypophosphatemic vitamin D dependent rickets and vitamin D dependent rickets;
  (vii) in the bone—anticonvulsant treatment, fibrogenisis imperfecta ossium, osteitits fibrosa cystica, osteomalacia, osteoporosis, osteopenia, osteosclerosis, renal osteodytrophy and rickets;
  (viii) in the intestine—glucocorticoid antagonism, idopathic hypercalcemia, malabsorption syndrome, steatorrhea and tropical sprue.

In one aspect, the present invention includes a method for inhibiting cell proliferation comprising administering an effective amount of a compound of the invention to a cell or animal in need thereof. Suitably, the invention includes a method of treating a cell proliferative disorder comprising administering an effective amount of a compound of the invention to a cell or animal in need thereof. The present invention also includes a use of a compound of the invention to treat a cell proliferative disorder. The present invention further includes a use of a compound of the invention to prepare a medicament to treat a cell proliferative disorder. As used herein, the term "cell proliferative disorder" refers to any disease or conditions which benefits from an inhibition of the proliferation of abnormal but not normal cells. Abnormal cells include any type of cell that is causative of or involved in a disease or condition and wherein it is desirable to modulate or inhibit the proliferation of the abnormal cell to treat the disease or condition. Examples of abnormal cells include malignant or cancerous cells as well as cell that over-proliferate in inflammatory conditions such as psoriasis. In an embodiment of the invention, the cell proliferative disorder is cancer, in particular breast, prostate, lung, colon, colorectal, kidney, head, neck or pancreatic cancer, Kaposi's sarcoma or leukemia.

The compounds of the invention can be used alone or contemporaneously with other agents that modulate CYP24 activity, or contemporaneously with other types of treatment (which may or may not modulate CYP24) for diseases that benefit from a modulation, suitably an increase, in the levels of 1α,25-dihydroxyvitamin $D_3$, or analogs thereof, and/or an inhibition of the catabolism of 1α,25-dihydroxyvitamin $D_3$, or an analog thereof. Suitably the compounds of the invention are administered contemporaneously with 1α,25-dihydroxyvitamin $D_3$ (calcitriol), an analog of 1α,25-dihydroxyvitamin $D_3$ or other vitamin D receptor agonists. Inhibiting catabolism of vitamin D receptor agonists such as 1α,25-dihydroxyvitamin $D_3$, or analogs thereof, will lengthen the biological lifetime or efficacy of these therapies and thus allow smaller amounts of the drug to be used for effective human chemotherapy; such smaller dosing will avoid, or at least minimize, the side effects, for example the hypercalcemic toxicity, associated with medicinal use of these compounds. The present invention therefore provides a method of increasing the efficacy of a vitamin D receptor agonist comprising contemporaneously administering an effective amount of a compound of the invention and an effective amount of the vitamin D receptor agonist. Further the invention includes the use of a compound of the invention to increase the efficacy of a vitamin D receptor agonist and a use of a compound of the invention to prepare a medicament to increase the efficacy of a vitamin D receptor agonist. In embodiments of the invention, the vitamin D receptor agonist is 1α,25-dihydroxyvitamin $D_3$, or an analog thereof. By analog of 1α,25-dihydroxyvitamin $D_3$, it is meant a chemically modified analog of 1α,25-dihydroxyvitamin $D_3$ which is a vitamin D receptor agonist and therefore exhibits a therapeutic profile similar to 1α,25-dihydroxyvitamin $D_3$. Examples of such compounds can be found in the following review articles, the contents of which are incorporated herein by reference: Pinette, K. V et al. "Vitamin D Receptor as a Drug Discovery Target", Mini Reviews in Med. Chem. 2003, 3:193-204; Mathieu, C. and Adorini, L. "The Coming of Age of 1,25-Dihydroxyvitamin $D_3$ Analogs as Immunomodulatory Agents", Trends in Mol. Med. 2002, 8:174-179; Carlberg, C. "Molecular Basis of the Selective Activity of Vitamin D Analogues", J. Cell. Bio. 2003, 88:274-281; Stein, M. S, and Wark, J. D. "An update on the therapeutic potential of vitamin D analogues", Expert Opin. Invest. Drugs 2003, 12:825-840; Bouillon, R. et al. "Structure-Function Relationships in the Vitamin D Endocrine System" Endocr. Rev. 1995, 16:200-257; and Nagpal, S. et al. "Vitamin D Analogs: Mechanism of Action and Therapeutic Applications", Current Med. Chem. 2001, 8:1661-1679.

It is to be understood that the compounds of the invention may also work by mechanisms other than CYP24 modulation. For example, the compounds of the invention, as analogs of 1α,25-dihydroxyvitamin $D_3$, also possess some of the intrinsic activity of 1α,25-dihydroxyvitamin $D_3$. For example, the compounds of the present invention have been shown to be able to activate the transcription of the CYP24 gene (see example 10). The compounds of the invention also possess vitamin D receptor agonist activity as evidenced by their ability to lower parathyroid hormone levels. Accordingly, the present invention also includes a method of treating conditions which benefit from administration of a vitamin D receptor agonist comprising administering to a subject in need thereof, an effective amount of a compound of the invention. The invention also includes the use of a compound of the invention to treat conditions which benefit from administration of a vitamin D receptor agonist and to prepare a medicament to treat conditions which benefit from administration of a vitamin D receptor agonist. Conditions which benefit from administration of a vitamin D receptor agonist include, for example cancer (such as breast cancer, lung cancer, prostate cancer, colon cancer, colorectal cancer, kidney cancer, head and neck cancer, pancreatic cancer, Kaposi's sarcoma and leukemia), dermatological conditions (such as psoriasis and wound healing), parathyroid disorders (such as hyperparathyroidism and secondary hyperparathyroidism), immunological disorders and bone disorders (such as osteoporosis).

Treatments used in combination or contemporaneously with the compounds of the present invention may be based on the disease type and do not have to specifically target CYP24 activity or the VDR. In a particular aspect of the present invention, the compounds of the invention are used in combination or contemporaneously with other therapies and therapeutics to treat dermatological disorders, bone disorders, parathyroid disorders, cancer and autoimmune disorders. Such therapies include, but are not limited to the following: for cancer: surgery, radiation, chemotherapies and biotherapies; for psoriasis: ultraviolet B radiation, chemotherapy and biotherapies.

In addition to cancer, the compounds of the invention are useful in treating other conditions involving aberrant or abnormal cell proliferation. Other cell proliferative disorders that may be treated by the present invention include inflammatory diseases, allergies, autoimmune disease, graft rejection, psoriasis, restenosis, artherosclerosis, and any other disorder wherein it is desirable to inhibit, prevent or suppress cell growth. Compounds of the invention may be tested for their efficacy in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; Psoriasis: International Archives of allergy and Immunology (2000) Volume 123 page 275. "T-cell receptor mimic peptides and their potential application in T-cell mediated disease" by A. H. Enk; and Secondary Hyperparathyroidism: Robinson, D. M. and Scott, L. J. "Paricalcitriol: A Review of its Use in the Management of Secondary Hyperparathyroidism", Drugs, 2005, 65:559-576.

The compounds of the invention are suitably formulated into pharmaceutical compositions for administration to human subjects in a biologically compatible form suitable for administration in vivo. Accordingly, in another aspect, the present invention provides a pharmaceutical composition comprising a compound of the invention, in admixture with a suitable diluent or carrier.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of Formula I may be used pharmaceutically in the form of the free base, in the form of salts, solvates and as hydrates. All forms are within the scope of the invention. Acid and basic addition salts may be formed with the compounds of the invention for use as sources of the free base form even if the particular salt per se is desired only as an intermediate product as, for example, when the salt is formed only for the purposes of purification and identification. All salts that can be formed with the compounds of the invention are therefore within the scope of the present invention.

In accordance with the methods of the invention, the described compounds of the invention, may be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of the invention, may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

The compounds of the invention, can be used alone or contemporaneously with other agents that modulate CYP24 activity or in combination with other types of treatment (which may or may not modulate CYP24) for cell proliferative disorders or other disorders that benefit from a modulation in the levels of 1α,25-dihydroxy vitamin $D_3$ and/or an inhibition of the catabolism of 1α,25-dihydroxy vitamin $D_3$. Suitably the compounds of the invention are administered contemporaneously with 1α,25-dihydroxy vitamin $D_3$ (calcitriol) or other vitamin D receptor agonists. Inhibiting catabolism of vitamin D receptor agonists will lengthen the biological lifetime or efficacy of these therapies and thus to allow smaller amounts of the drug to be used for effective human chemotherapy; such smaller dosing will avoid, or at least minimize, the hypercalcemic toxicity associated with medicinal use of calcitriol or other vitamin D receptor agonists. The present invention therefore includes a method of increasing the efficacy of a vitamin D receptor agonist, suitably 1α,25-dihydroxy vitamin $D_3$ (calcitriol), comprising contemporaneously administering an effective amount of a compound of the invention and an effective amount of the vitamin D receptor agonist, suitably 1α,25-dihydroxy vitamin $D_3$ (calcitriol). Further the invention includes a use of a compound of the invention to increase the efficacy of a vitamin D receptor agonist, suitably 1α,25-dihydroxy vitamin $D_3$ (calcitriol), and a use of a compound of the invention to prepare a medicament to increase the efficacy of a vitamin D receptor agonist, suitably 1α,25-dihydroxy vitamin $D_3$ (calcitriol).

In a further aspect of the present invention, the compounds of the invention may be used in combination or contemporaneously with other therapies and therapeutics to treat dermatological disorders, bone disorders, parathyroid disorders, immunological disorders, wound healing and osteoporosis.

In addition to the above-mentioned therapeutic uses, the compounds of the invention are also useful in diagnostic assays, screening assays and as research tools.

In diagnostic assays the compounds of the invention may be useful in identifying or detecting a cell proliferative disorder. In such an embodiment, the compounds of the invention may be radiolabelled (as hereinbefore described) and contacted with a population of cells. The presence of the radiolabelled on the cells may indicate a cell proliferative disorder.

In screening assays, the compounds of the invention may be used to identify other compounds that modulate cell proliferation or CYP24 activity. As research tools, the compounds of the invention may be used in receptor binding assays and assays to study the localization of CYP24. In such assays, the compounds may also be radiolabelled.

The following non-limiting examples are illustrative of the present invention:

EXAMPLES

Materials and Methods

Unless otherwise noted, all reactions were performed in oven-dried glassware stirred under an atmosphere of ultra-high-purity argon. THF was distilled from Na/benzophenone ketyl immediately prior to use. Organolithiums were titrated prior to use following known methods (Suffert, J. *J. Org. Chem.* 1989, 54, 509-510). Methylene chloride ($CH_2Cl_2$) and triethylamine ($Et_3N$) were distilled from calcium hydride prior to use. All other reagents were used as received from commercial suppliers. Analytical TLC analysis was conducted on precoated glass-backed silica gel plates (Merck Kieselgel 60 $F_{254}$, 250 mm thickness) and visualized with p-anisaldehyde or $KMnO_4$ stains. Column chromatography was performed using short path silica gel (particle size <230 mesh) or flash silica gel (particle size 230-400 mesh). Preparative-plate chromatography was performed using silica-gel-coated glass preparative plates (500-1000 μm) from Analtech and analyzed by UV. High-performance liquid chromatography (HPLC) was carried out using a Rainin HPLX system equipped with two 25-mL/min preparative pump heads using Rainin Dynamax 10-mm×250-mm (semi-preparative) columns packed with 60 Å silica gel (8 μm pore size) as C-18-bonded silica and a Rainin Dynamax UV-C dual-beam variable-wavelength detector set at 265 nm. Yields are reported for pure products (>95% based on their chromatographic and spectroscopic homogeneity) and are unoptimized. Optical rotations were measured at the Na line using a Perkin-Elmer 141 Polarimeter. Nuclear magnetic resonance (NMR) spectra were obtained on a Varian XL-400 spectrometer operating at 400 MHz for $^1H$, and 100 MHz for $^{13}C$. Chemical shifts are reported in ppm (δ) and are referenced to $CDCl_3$ (7.26 ppm for $^1H$ and 77.0 ppm for $^{13}C$), and tetramethylsilane (TMS, 0.00 ppm for $^1H$). Ultraviolet (UV) spectra were obtained using a Cary Bio 400 spectrophotometer at ambient temperature. Infrared specta (IR) spectra were obtained using a Perkin Elmer 1600 Series FT-IR instrument. Absorption bands are reported in wavenumbers ($cm^{-1}$). Low and high resolution mass spectra (LRMS and HRMS) were obtained with electronic of chemical ionization (EI or CI) at the mass spectrometry facility at the Ohio State University on a Micromass QTOF Electrospray mass spectrometer.

Example 1

Synthesis of Compound (20R)-I(a)

(i) Preparation of Ketone VII(a) ($R^1=CF_3$)

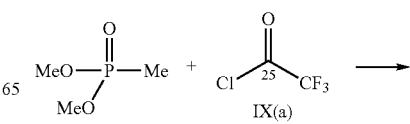

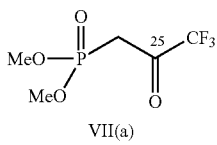

VII(a)

To a stirred solution of dimethyl methyl phosphonate (10 g, 0.08064 mol) in 400 ml THF was added under nitrogen a solution of n-BuLi in hexanes (75.6 ml, 1.6 M, 0.12096 mol) at −78° C. After complete addition, the reaction mixture was stirred for 75 min at −78° C. A solution of trifluoroacetyl chloride IX(a) (25.4 g, 0.1209523 mol) in 100 ml THF was added at −78° C. After complete addition, the reaction mixture was stirred for 90 min at −78° C., then poured into 100 ml of water. THF was removed under vacuum and the residue was saturated with brine and extracted with ethyl acetate (150 ml, 100 ml). The combined organic layers were washed with water, dried with $Na_2SO_4$ and concentrated in vacuum. The residue was purified by column chromatography (ethyl acetate, hexane) furnishing ketone VII(a) ($R^1$=$CF_3$) (10.64 g, 60%). $^1$H NMR ($CDCl_3$, 200 MHz): δ 3.87 (3H, s), 3.83 (3H, s), 2.41 (1H, s), 2.83 (1H, s); Mass (m/z): 221.0 ($M^+$, 100%).

(ii) Preparation of Oxime V(a) ($R^1$=$CF_3$, $R^2$=$CH_3$)

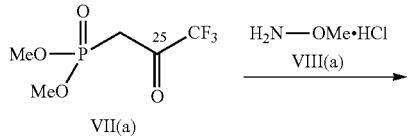

Ketone VII(a) ($R^1$=$CF_3$) (5 g, 0.02272 mol) was dissolved in 20 ml pyridine and added methoxylamine hydrochloride VIII(a) (2.277 g, 0.02727 mol) under nitrogen atmosphere. The reaction mixture was stirred for 7 days at room temperature. After completion of the reaction, water was added and extracted with ethyl acetate (150 ml, 100 ml). The combined organic layers were washed with water, dried $Na_2SO_4$ and concentrated in vacuum furnishing oxime V(a) ($R^1$=$CF_3$, $R^1$=$CH_3$) (3.67 g, 65%). $^1$H NMR ($CDCl_3$, 200 MHz) δ 3.84 (3H, s), 3.82 (3H, s), 3.79 (3H, s), 2.44 (1H, s), 2.24 (1H, s); Mass (m/z): 251.1 ($M^+$, 100%).

(iii) Preparation of CD-ring Oxime IV(a) ($R^1$=$CF_3$, $R^2$=$CH_3$, PG=TBS)

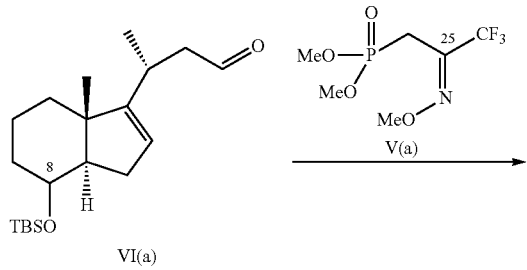

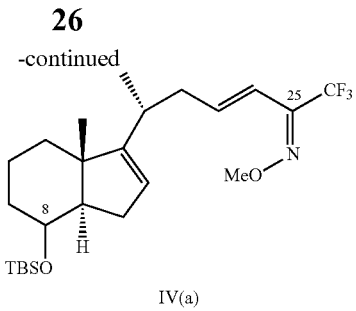

IV(a)

KOtBu (0.4999 g, 0.004464 mol) was dissolved in 15 ml of THF under nitrogen and cooled to 0° C. A solution of phosphonic ester V(a) (1.111 g, 0.004464 mol) in THF (10 ml) was added at 0° C. and the yellow solution was stirred for 30 min. Then, a solution of CD-ring aldehyde VI(a) (1 g, 0.002976 mol) in 15 ml THF was added at 0° C. After complete addition, the ice bath was removed and the reaction mixture was stirred for 4 h at room temp. After complete conversion, the reaction mixture was poured into 75 ml water and extracted with ethyl acetate (100 ml). The combined organic layers were washed with water, dried and concentrated in vacuum. The residue was purified by column chromatography furnishing oxime IV(a) ($R^1$=$CF_3$, $R^2$=$CH_3$, PG=TBS) (1.1 g, 80.4%). $^1$H NMR ($CDCl_3$, 200 MHz) δ 6.43 (2H, m), 5.31 (1H, m), 4.12 (1H, m), 4.01 (3H, s), 2.45-1.21 (12H, m), 1.07 (3H, d, J=3.5 Hz), 0.94 (12H, m), 0.01 (6H, s); Mass (m/z): 460.1 ($M^+$, 100%).

(iv) Preparation of CD-Ring Ketone II(a) ($R^1$=$CF_3$, $R^2$=$CH_3$)

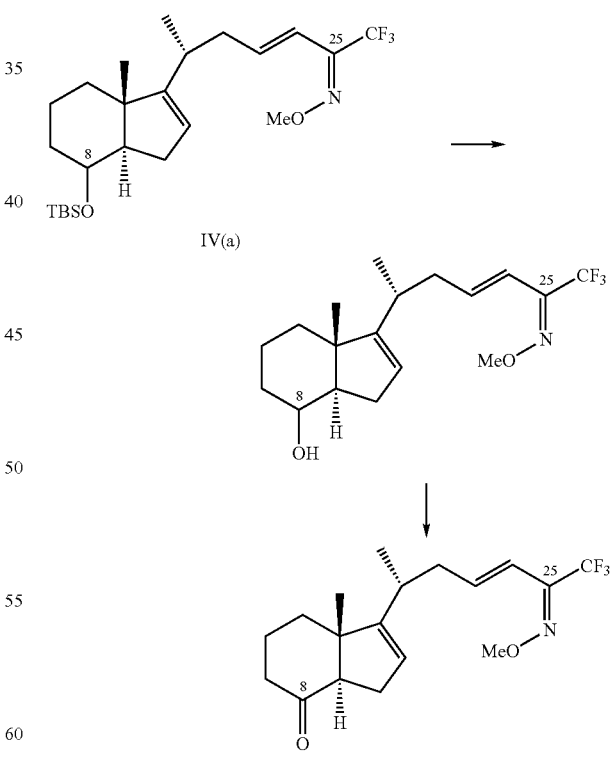

TBAF solution (3.16 ml, 1M solution in THF) was added drop wise to oxime IV(a) ($R^1$=$CF_3$, $R^2$=$CH_3$, PG=TBS) (580 mg, 0.001026 mol) and stirred for 10 h at RT. After complete conversion, water 75 ml was added and extracted with ethyl acetate (150 ml, 100 ml). The combined organic layers were washed with water, dried and concentrated in vacuum. The residue was purified by column chromatography furnishing the deprotected product (326 mg, 78.8%). $^1$H NMR (CDCl$_3$, 200 MHz) δ 6.41 (2H, m), 5.37 (1H, m), 4.14 (1H, m), 4.01 (3H, s), 2.45-1.10 (12H, m), 1.02 (3H, d, J=3.5 Hz), 0.80 (3H, s); Mass (m/z): 346.4 (M$^+$, 100%).

To a solution of the deprotected product (220 mg, 0.00063 mol) in 15 ml CH$_2$Cl$_2$, PDC (575 mg, 0.00153 mol) and oven-dried Celite (500 mg) were added and the mixture was stirred for 16 h, during which the color of the suspension changed from orange to brown. Et$_2$O was added and the mixture was filtered over Celite. The residue was extracted with Et$_2$O (2×100 ml) and the combined organic layers were dried over Na$_2$SO$_4$ and the volatiles were removed in vacuum and the residue was purified by column chromatography furnishing CD-ring ketone II(a) (R$^1$=CF$_3$, R$^2$=CH$_3$) (165 mg, 75.4%). $^1$H NMR (CDCl$_3$, 200 MHz) δ 6.45 (2H, m), 5.32 (1H, m), 4.03 (3H, s), 2.85 (1H, m), 2.57-1.75 (11H, m), 1.61-0.75 (6H, m); Mass (m/z): 344.1 (M$^+$, 100%).

(v) Preparation of Compound (20R)-I(a)

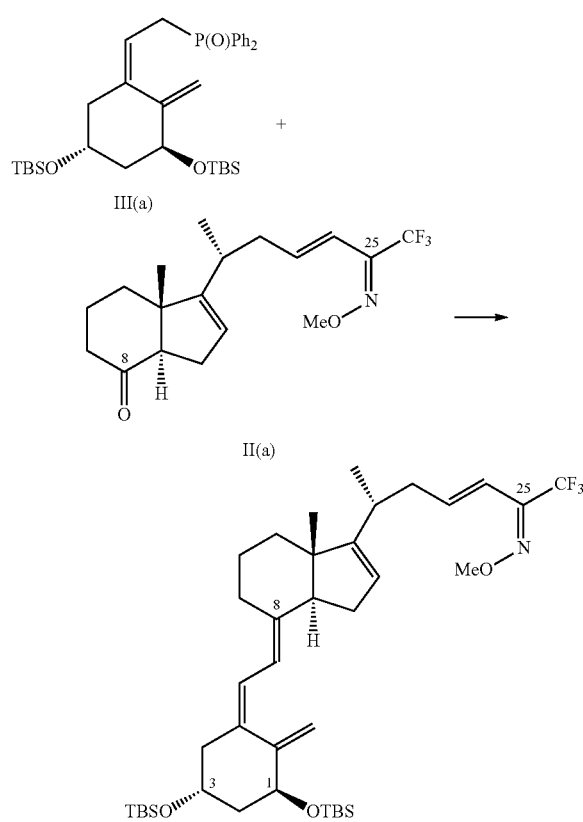

To a stirred solution of A-ring phosphineoxide III(a) (R$^3$=OTBS, R$^4$=CH$_2$, PG=TBS) (440 mg, 0.000746 mol) in 5 ml THF was added a solution of n-BuLi in hexanes (1.6M, 0.466 ml, 0.000746 mol) at −78° C. and the deep red colored solution was stirred for 20 min. Then, a solution of CD-ring ketone II(a) (R$^1$=CF$_3$, R$^2$=CH$_3$) (80 mg, 0.0002332 mol) in 4 ml THF was added at −78° C. The reaction mixture was stirred for 1 hr at −78° C. After complete conversion, 10 ml of 20% Na—K tartrate was added, and extracted with ethyl acetate (2×75 ml). The combined organic layers were washed with water, dried over Na$_2$SO$_4$ and concentrated in vacuum. The residue was purified by column chromatography furnishing the TBS-protected compound (20R)-I(a) (120 mg, 72.6%).

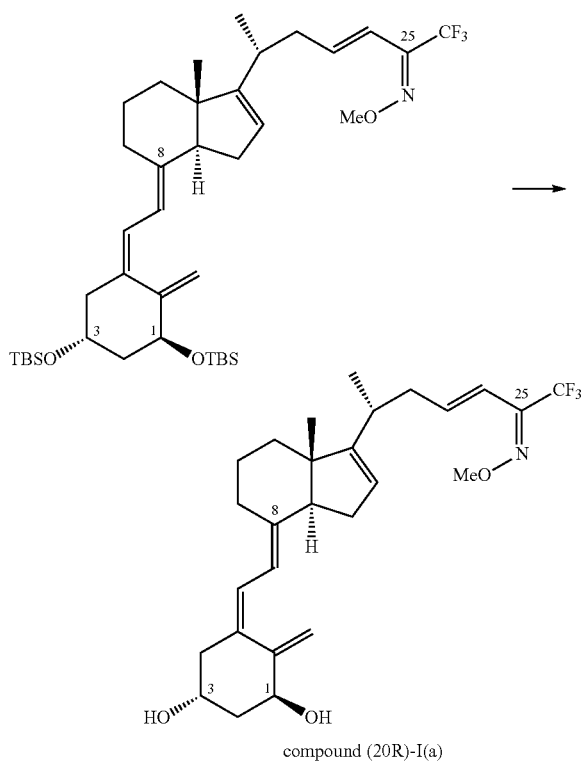

compound (20R)-I(a)

20 TBAF solution (0.254 ml, 1M in THF, 0.00002542 mol) was added drop wise to TBS-protected compound (20R)-I(a) (60 mg, 0.0000847 mol) and stirred for 10 h at RT. After complete conversion, water (30 ml) was added and extracted with ethyl acetate (2×50 ml). The combined organic layers were washed with water and over Na$_2$SO$_4$. Initially the residue was purified by column chromatography and later purified by preparative HPLC to provide compound (20R)-I(a) (6 mg). $^1$H NMR (CDCl$_3$, 200 MHz) δ 6.41 (3H, m), 6.11 (1H, d, J=11 Hz), 5.34 (2H, m), 5.01 (1H, s), 4.46 (1H, m), 4.22 (1H, m), 4.05 (3H, s), 2.81 (1H, m), 2.62 (1H, m), 2.45-1.46 (15H, m), 1.12 (3H, d, J=3.5 Hz), 0.68 (3H, s); Mass (m/z): 480.3 (M$^+$, 20%); 462.0 (M+−H$_2$O, 50%), 148.9 (100%). HPLC purity 89.6% (RT 34.457 min), Zorbax-SB-C18 150× 4.6 mm, 3.5 microns, 266 nm, Ammonium acetate: Water: Methanol: Acetonitrile (Gradient).

Example 2

Synthesis of Compound (20R)-I(c)

(i) Preparation of Ketone VII (R$^1$=cyclopropane)

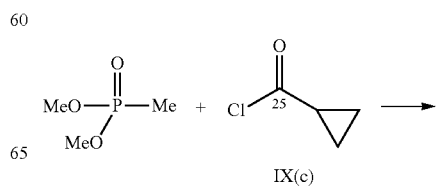

IX(c)

-continued

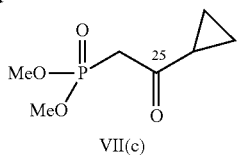
VII(c)

To a stirred solution of dimethyl methyl phosphonate (10 g, 0.08064 mol) in 400 ml THF was added under nitrogen a solution of n-BuLi in hexanes (75.6 ml, 1.6 M, 0.12096 mol) at −78° C. After complete addition, the reaction mixture was stirred for 75 min at −78° C. A solution of cyclopropyl carbonyl chloride IX(c) (12.6 ml, 0.12096) in 100 ml THF was added at −78° C. After complete addition, the reaction mixture was stirred for 90 min at −78° C., then poured into 100 ml water. THF was removed under vacuum and the residue was saturated with brine and extracted with ethyl acetate (150 ml, 100 ml). The combined organic layers were washed with water, dried with $Na_2SO_4$ and concentrated in vacuum. The residue was purified by column chromatography (ethyl acetate, hexane) furnishing ketone VII(c) ($R^1$=cyclopropane) as yellow oil (7 g, 45.2%). $^1H$ NMR ($CDCl_3$, 200 MHz) δ 3.88 (3H, s), 3.80 (3H, s), 3.28 (1H, s), 3.19 (1H, s), 2.17 (1H, m), 1.18-0.93 (4H, m); Mass (m/z): 193.0 ($M^+$, 100%).

(ii) Preparation of Oxime V(c) ($R^1$=cyclopropane, $R^2$=$CH_3$)

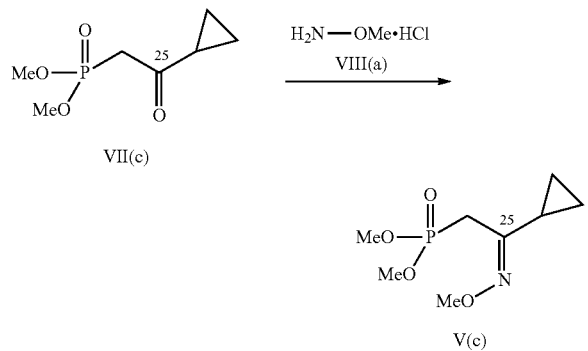

Ketone VII(c) ($R^1$=cyclopropane) (5 g, 0.02604 mol) was dissolved in 20 ml pyridine and added methoxylamine hydrochloride VIII(a) (2.50125 g, 0.0299 mol) under nitrogen atmosphere. The reaction mixture was stirred for 7 days at room temperature. After completion of the reaction, water was added and extracted with ethyl acetate (150 ml, 100 ml). The combined organic layers were washed with water, dried $Na_2SO_4$ and concentrated in vacuum furnishing oxime V(c) ($R^1$=cyclopropane, $R^2$=$CH_3$) (3.5 g 60.8%). $^1H$ NMR ($CDCl_3$, 200 MHz) δ 3.82 (3H, s), 3.80 (3H, s), 3.76 (3H, s), 3.17 (1H, s), 2.94 (1H, s), 1.63 (1H, m), 0.91 (4H, m); Mass (m/z): 221.9 ($M^+$, 100%).

(iii) Preparation of CD-Ring Oxime IV(c) ($R^1$=Cyclopropane, $R^2$=$CH_3$, PG=TBS)

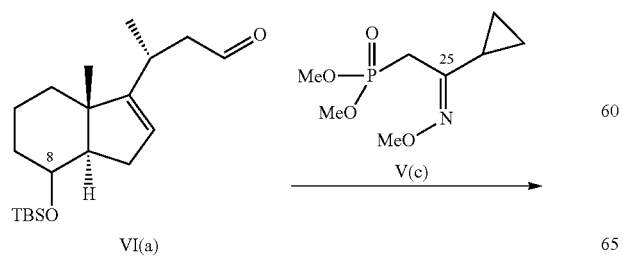

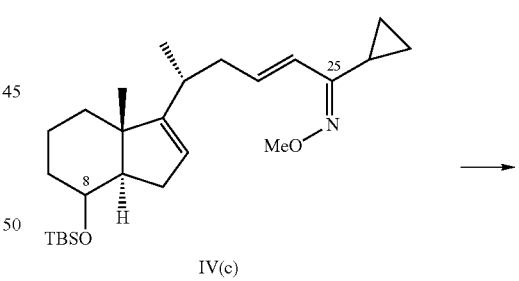
IV(c)

KOtBu (0.4999 g, 0.004464 mol) was dissolved in 15 ml of THF under nitrogen and cooled to 0° C. A solution of phosphonic ester V(c) (0.9866 g 0.004464 mol) in THF (10 ml) was added at 0° C. and the yellow solution was stirred for 30 min. Then, a solution of CD-Ring aldehyde VI(a) (1 g, 0.002976 mol) in 15 ml THF was added at 0° C. After complete addition, the ice bath was removed and the reaction mixture was stirred for 4 h at room temp. After complete conversion, the reaction mixture was poured into 75 ml water and extracted with ethyl acetate. (100 ml). The combined organic layers were washed with water, dried and concentrated in vacuum. The residue was purified by column chromatography furnishing oxime IV(c) ($R^1$=cyclopropane, $R^2$=$CH_3$, PG=TBS) (1 g, 78.7%). $^1H$ NMR ($CDCl_3$, 200 MHz) δ 6.65 (1H, d, J=16.5 Hz), 6.41 (1H, m), 5.31 (1H, m), 4.15 (1H, m), 3.82 (3H, s), 2.45-1.21 (12H, m), 1.07 (3H, d, J=3.5 Hz), 0.94 (13H, m), 0.73 (3H, m), 0.01 (6H, s); Mass (m/z): 432.1 ($M^+$, 100%).

(iv) Preparation of CD-Ring Ketone II(c) ($R^1$=cyclopropane, $R^2$=$CH_3$)

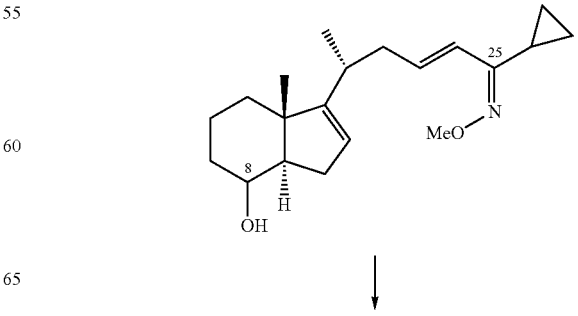

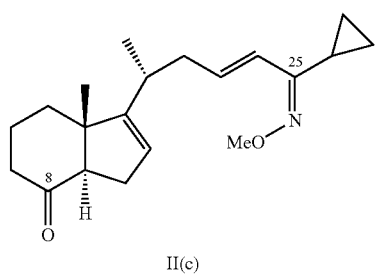

II(c)

TBAF solution (3.48 ml, 1M solution in THF) was added drop wise to oxime IV(c) (R$^1$=cyclopropane, R$^2$=CH$_3$, PG=TBS) (600 mg, 0.001392 mol) and stirred for 10 h at RT. After complete conversion, water 75 ml was added and extracted with ethyl acetate (150 ml, 100 ml). The combined organic layers were washed with water, dried and concentrated in vacuum. The residue was purified by column chromatography furnishing the deprotected product (360 mg, 81.5%). $^1$H NMR (CDCl$_3$, 200 MHz) δ 6.63 (1H, d, J=16.5 Hz), 6.38 (1H, m), 5.37 (1H, m), 4.19 (1H, m), 3.80 (3H, s), 2.45-1.10 (12H, m), 1.02 (7H, m), 0.80 (3H, m); Mass (m/z): 318.1 (M$^+$, 100%).

To a solution of the deprotected product (240 mg, 0.00075 mol) in 15 ml CH$_2$Cl$_2$, PDC (683.5 mg, 0.001817 mol) and oven-dried Celite (500 mg) were added and the mixture was stirred for 16 h, during which the color of the suspension changed from orange to brown. Et$_2$O was added and the mixture was filtered over Celite. The residue was extracted with Et$_2$O (2×100 ml) and the combined organic layers were dried over Na$_2$SO$_4$ and the volatiles were removed in vacuum and the residue was purified by column chromatography furnishing of CD-ring ketone II(c) (R$^1$=cyclopropane, R$^2$=CH$_3$) (202 mg, 84.7%). $^1$H NMR (CDCl$_3$, 200 MHz) δ 6.66 (1H, d, J=16.5 Hz), 6.39 (1H, m), 5.37 (1H, m), 3.83 (3H, s), 2.85 (1H, m), 2.57-1.75 (13H, m), 1.61-0.75 (9H, m); Mass (m/z): 316.1 (M$^+$, 100%).

(v) Preparation of Compound (20R)-I(c)

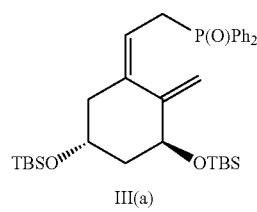

III(a)

+

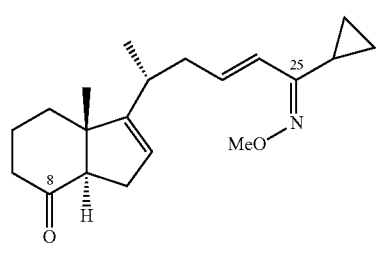

II(c)

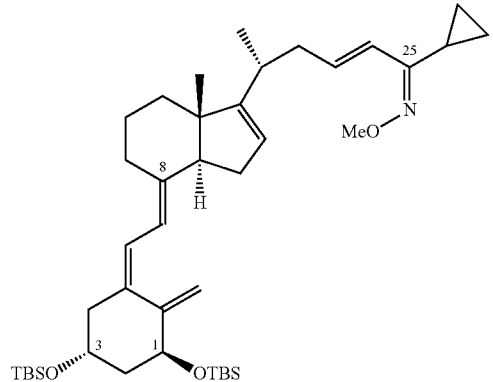

To a stirred solution of A-ring phosphineoxide 111(a) (R$^3$=OTBS, R$^4$=CH$_2$, PG=TBS) (559.7 mg, 0.001015 mol) in 5 ml THF was added a solution of n-BuLi in hexanes (1.6M, 0.6349 ml, 0.001015 mol) at −78° C. and the deep red colored solution was stirred for 20 min. Then, a solution of CD-ring ketone II(c) (R$^1$=cyclopropane, R$^2$=CH$_3$) (100 mg, 0.0003174 mol) in 4 ml THF was added at −78° C. The reaction mixture was stirred for 1 hr at −78° C. After complete conversion, 10 ml of 20% Na—K tartrate was added, and extracted with ethyl acetate (2×75 ml). The combined organic layers were washed with water, dried over Na$_2$SO$_4$ and concentrated in vacuum. The residue was purified by column chromatography furnishing TBS-protected compound (20R)-I(c) (160 mg, 74.2%).

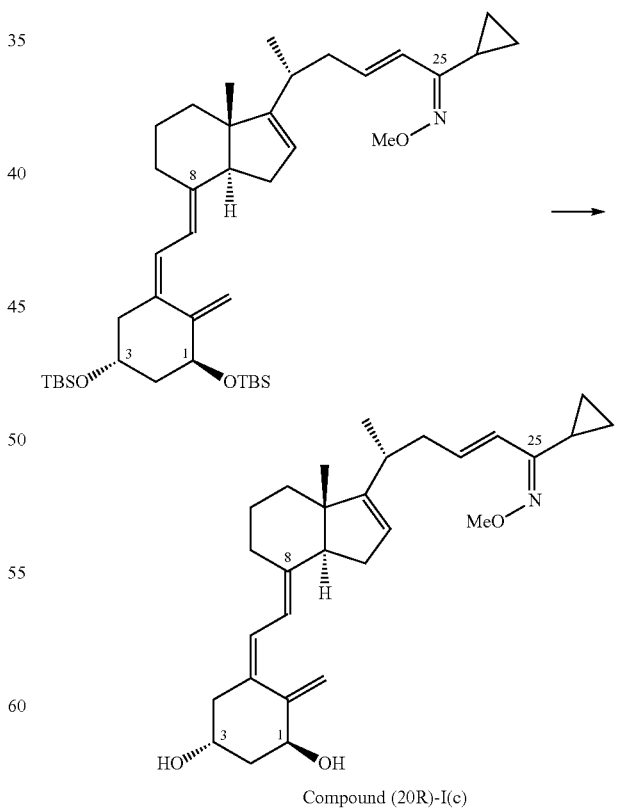

Compound (20R)-I(c)

TBAF solution (0.3976 ml, 1M in THF, 0.0003976 mol) was added drop wise to TBS-protected compound (20R)-I(c)

(90 mg, 0.0001325 mol) and stirred for 10 h at RT. After complete conversion, water (30 ml) was added and extracted with ethyl acetate (2×50 ml). The combined organic layers were washed with water and over Na$_2$SO$_4$. Initially the residue was purified by column chromatography and later purified by preparative HPLC to provide compound (20R)-I(c) (14 mg). $^1$H NMR (CDCl$_3$, 200 MHz) δ 6.66 (1H, d, J=16.5 Hz), 6.39 (2H, m), 6.11 (1H, d, J=11 Hz), 5.34 (2H, m), 5.02 (1H, s), 4.44 (1H, m), 4.23 (1H, m), 3.82 (3H, s), 2.81 (1H, m), 2.62 (1H, m), 2.45-1.46 (15H, m), 1.12 (3H, d, J=3.5 Hz), 0.93-0.84 (7H, m); Mass (m/z): 452.3 (M$^+$, 100%). HPLC purity 93.76% (R$_T$ 32.074 min), Zorbax-SB-C18 150×4.6 mm, 3.5 microns, 220 nm, Ammonium acetate: Water: Methanol: Acetonitrile (Gradient).

Example 3

Synthesis of Compound I(e)

(i) Preparation of Ketone VII(e) (R$^1$=t-Butyl)

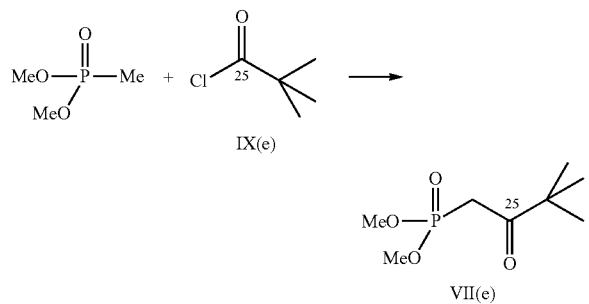

A 100 mL recovery flask was charged with dimethyl-methylphosphonate (1.0 g, 8.1 mmol) and dissolved in 40 mL of distilled THF. This solution was cooled to −78° C. and n-butyllithium (7.5 mL of 1.6 M solution, 12.0 mmol, 1.5 eq.) was added via syringe. This mixture was then allowed to stir at this temperature for 1 h. Pivaloyl chloride (IX(e), R$^1$=t-butyl) (1.45 g, 12.0 mmol, 1.5 eq.) was dissolved in 10 mL of distilled THF and cooled to −78° C. and added to the mixture over 15 minutes. The reaction was monitored by TLC. The mixture was then rinsed into a separatory funnel with ethyl acetate and extracted with ethyl acetate (3×50 mL). Combined extracts were washed with water (2×50 mL), brine solution (1×25 mL), dried over Na$_2$SO$_4$ and filtered. The filtrate was concentrated in vacuo to give the crude product. This crude product was purified by column chromatography (0-10% methanol/ethyl acetate) to afford VIII(e) (R$^1$=t-butyl) (1.2 g, 70%). $^1$H NMR (CDCl$_3$, 400 MHz): δ 3.81 (s, 3H), 3.80 (s, 3H), 3.18 (d, 2H, J$_{CP}$=21.6 Hz), 1.18 (s, 9H); $^{13}$C NMR (CDCl$_3$, 100 MHz): δ 207.3 (d, J$_{CP}$=29.2 Hz), 52.9 (d, J$_{CP}$=25.6 Hz), 45.3 (d, J$_{CP}$=16.4 Hz), 35.6, 34.3, 25.9; HRMS: calcd for C$_8$H$_{17}$O$_4$PNa$^+$[M+Na]: 231.0756. found: 231.0747.

(ii) Preparation of Oxime V(e) (R$^1$=t-Butyl, R$^2$=CH$_3$)

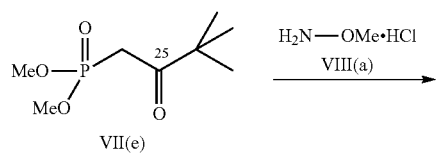

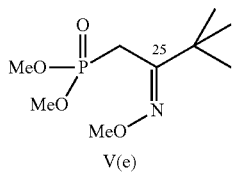

A 10 mL recovery flask was charged with phosphonate VII(e) (R$^1$=t-butyl) (0.20 g, 0.96 mmol) and dissolved in 1.9 mL of anhydrous pyridine. O-methylhydroxylamine hydrochloride (VIII(a), R$^2$=CH$_3$) (96 mg, 1.1 mmol, 1.15 eq.) and 4 Å powdered molecular sieves (500 mg/mmol of ketone) were added to the reaction flask this solution was left to stir at room temperature for 48 hours. The reaction was monitored by TLC. The mixture was then rinsed into a separatory funnel with ether and extracted with ether (3×25 mL). Combined extracts were washed with water (1×25 mL), brine solution (1×25 mL), dried over Na$_2$SO$_4$ and filtered. The filtrate was concentrated in vacuo to give the crude product which product was purified by column chromatography (100% ethyl acetate) to afford V(e) (0.176 g, 77%). $^1$H NMR (CDCl$_3$, 400 MHz): δ 3.80 (s, 3H), 3.69 (s, 3H), 3.67 (s, 3H), 2.90 (d, 2H, J$_{CP}$=24 Hz), 1.11 (s, 9H); $^{13}$C NMR (CDCl$_3$, 100 MHz): δ 157.6 (d, J$_{CP}$=42 Hz), 61.3, 52.6 (d, J$_{CP}$=25.6 Hz), 36.9 (d, J$_{CP}$=8.4 Hz), 27.8, 24.8, 23.4; HRMS: calcd for C$_9$H$_{20}$O$_4$PNa$^+$[M+Na]: 260.1022. found: 260.1019.

(iii) Preparation of CD-Ring Oxime IV(e) (R$^1$=t-Butyl, R$^2$=CH$_3$)

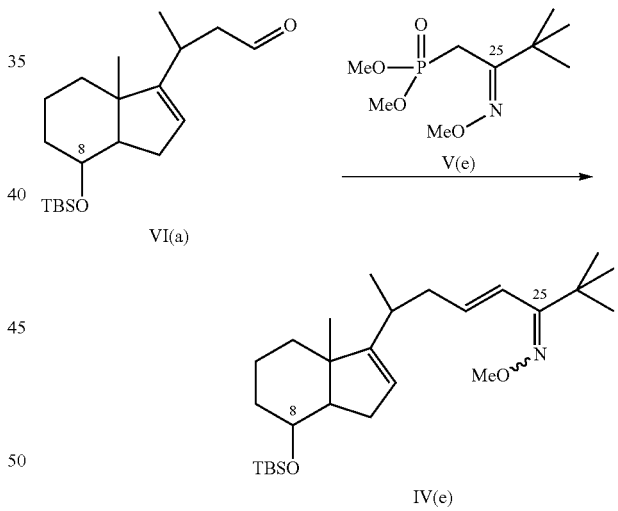

A 10 mL recovery flask was charged with potassium t-butoxide (9.0 mg, 0.082 mmol, 1.1 eq.) dissolved in 0.7 mL distilled THF and cooled to 0° C. Oxime V(e) (R$^1$=t-butyl, R$^2$=CH$_3$) (20 mg, 0.082 mmol, 1.1 eq.) was added as a solution in 0.5 mL distilled THF. This solution was left to stir for 30 minutes. Aldehyde VI(a) (25 mg, 0.074 mmol) in 1 mL of distilled THF was then added to the reaction mixture over several minutes via cannula at 0° C. After the addition was complete, the mixture was gradually warmed up to room temperature and then stirred for about 4 hours. TLC showed the complete consumption of starting material. The reaction was quenched by addition of 5 mL distilled water and then rinsed into a separatory funnel with ethyl acetate. The mixture was extracted with ethyl acetate (3×10 mL). The combined extracts were washed with water (1×10 mL), brine solution (1×10 mL), dried over Na$_2$SO$_4$ and filtered. The filtrate was concentrated in vacuo to give the crude product that was purified by flash column chromatography (0-10% ethyl acetate/hexanes) to give a viscous oil. A polypropylene vial was charged with this oil (20 mg, 0.045 mmol) dissolved in 1.0 mL anhydrous acetonitrile. To this solution was added 0.18 mL of HF (4.4 mmol, 49% aqueous solution, 98 eq.) via syringe at room temperature and the mixture was then allowed to stir at room temperature for 1 h. TLC showed the completion of the reaction. This reaction mixture was diluted with ether (25 mL) and saturated solution of NaHCO$_3$ was added until no more carbon dioxide was liberated. The reaction mixture was then rinsed into a separatory funnel with ethyl acetate and was extracted with ethyl acetate (4×25 mL). The combined extracts were washed with water (1×25 mL), and brine solution (1×25 mL), dried over Na$_2$SO$_4$ and filtered. The filtrate was concentrated in vacuo to give the crude product as a mixture of E and Z in 2:1 ratio. The crude was purified by column chromatography (0-10% ethyl acetate/hexanes) to afford 8 mg pure E isomer and 3 mg of Z isomer (74% overall). [α]$^{25}_D$=+ 5.4 (c 0.67, CHCl$_3$) $^1$H NMR (CDCl$_3$, 400 MHz): δ 6.36-6.28 (m, 1H), 5.92 (d, 1H, J=16.0 Hz), 5.35-5.34 (m, 1H), 4.18 (br, 1H), 3.82 (s, 3H), 2.42-2.16 (m, 4H), 2.01-1.71 (m, 5H), 1.58-1.37 (m, 4H), 1.14 (s, 9H), 1.03 (s, 3H), 1.02 (d, 3H, J=6.4 Hz); $^{13}$C NMR (CDCl$_3$, 100 MHz): δ 160.5, 159.3, 139.9, 120.6, 119.8, 69.2, 61.5, 54.3, 46.4, 41.2, 36.9, 35.4, 33.9, 31.7, 30.2, 28.7, 21.8, 18.3, 17.8; IR (3443 (m), 2954 (s), 2928 (s), 2860 (s), 1457 (m), 1364 (w), 1143 (w), 1053 (s), 998 (w), 890 (m) cm$^{-1}$; HRMS: calcd for C$_{21}$H$_{35}$NO$_2$Na$^+$[M+Na]: 356.2559. found: 356.2546.

(iv) Preparation of CD-Ring Ketone II(e) (R$^1$=t-Butyl, R$^2$=CH$_3$)

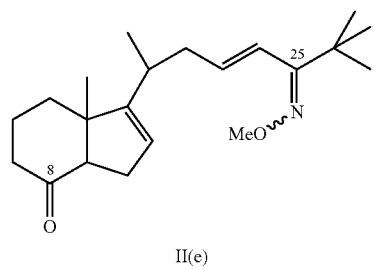

II(e)

A 10-mL recovery flask was charged with CD-ring oxime IV(e) (R$^1$=t-butyl, R$^2$=CH$_3$) (10 mg, 0.03 mmol) dissolved in 0.6 mL distilled CH$_2$Cl$_2$. To this solution was added pyridinium dichromate (24 mg, 0.071 mmol, 2.4 eq) and 15 mg of oven-dried Celite in one portion at room temperature. After stirring at room temperature for 12 hours, TLC showed the complete consumption of starting material. The mixture was directly purified by column chromatography (0-10% ethyl acetate/hexanes) to give CD-ring ketone II(e) (7.8 mg, 79%). [α]$^{25}_D$=+ 11.8 (c 0.4, CHCl$_3$). $^1$H NMR (CDCl$_3$, 400 MHz): δ 6.34-6.26 (m, 1H), 5.89 (d, 1H, J=16.4 Hz), 5.33-5.32 (m, 1H), 3.82 (s, 3H), 2.86 (dd, 1H, J=6.4, 10.4 Hz), 2.48-2.37 (m, 2H), 2.32-2.20 (m, 4H), 2.16-1.89 (m, 4H), 1.83-1.78 (m, 1H), 1.14 (s, 9H), 1.08 (s, 3H, J=6.8 Hz), 0.81 (s, 3H); $^{13}$C NMR (CDCl$_3$, 100 MHz): δ 211.0, 160.3, 157.1, 139.4, 121.0, 120.2, 63.1, 61.5, 53.8, 41.0, 40.5, 36.9, 34.4, 32.6, 28.6, 27.1, 24.0, 21.4, 17.2; IR: 2954 (s), 2931 (s), 2895 (s), 1713 (s), 1454 (m), 1372 (w), 1202 (w), 1055 (s), 978 (w) cm$^{-1}$; HRMS: calcd for C$_{21}$H$_{33}$NO$_2$Na$^+$[M+Na]: 354.2403. found: 354.2427.

(v) Preparation of Compound I(e)

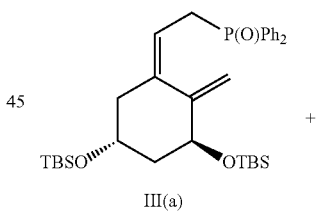

III(a)

+

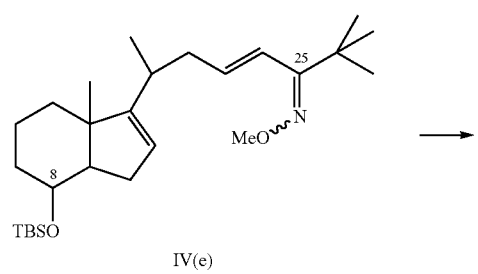

IV(e)

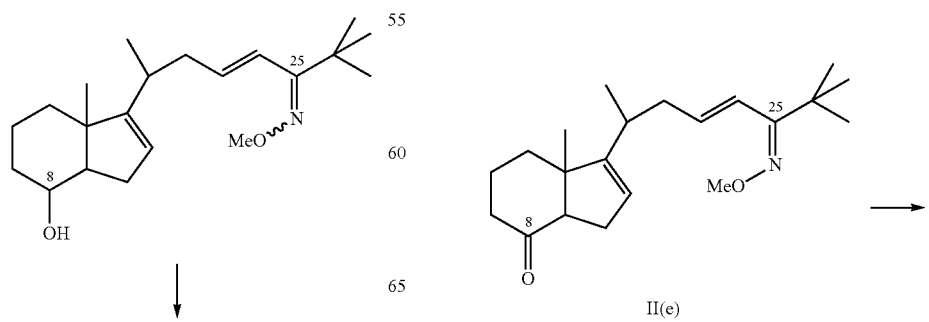

II(e)

37
-continued

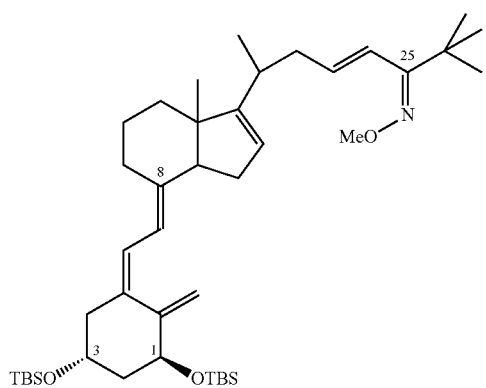

38
-continued

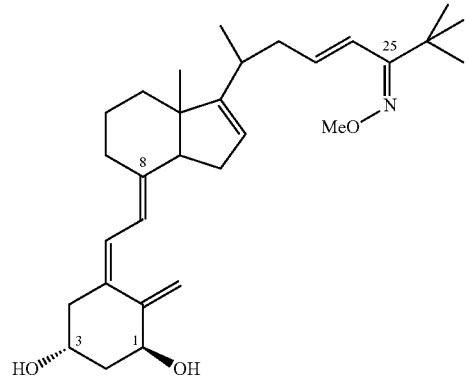

Compound I(e)

A 10 mL recovery flask was charged with anhydrous phosphine oxide III(a) (R³=O-tributylsilyl (OTBS), R⁴=CH₂) (45 mg, 0.077 mmol, 3.2 eq.) dissolved in distilled THF and cooled to −78° C. n-Butyllithium (48 μL of a 1.6M solution in hexanes, 0.077 mmol, 3.2 eq.) was added dropwise via syringe over several minutes resulting in a deep red color. This solution was left to stir for 10 min. Anhydrous CD-ring ketone II(e) (R¹=t-butyl, R²=CH₃) (8 mg, 0.024 mmol) was dissolved in 1 mL distilled THF and cooled to −78° C. This solution was then added to the reaction mixture via cannula, and the red colour persisted. This solution was stirred at −78° C. for 3 hours at which point it was quenched at −78° C. by addition of 5 mL of pH 7 buffer and allowed to come to room temperature. The mixture was then rinsed into a separatory funnel with ethyl acetate and extracted with ethyl acetate (3×25 mL). The combined extracts were washed with water (1×25 mL), brine solution (1×25 mL), dried over Na₂SO₄ and filtered. The filtrate was concentrated in vacuo to give the crude product which was briefly purified by preparative TLC plate (0-10% ethyl acetate/hexanes buffered with 1% Et₃N) to give a viscous oil.

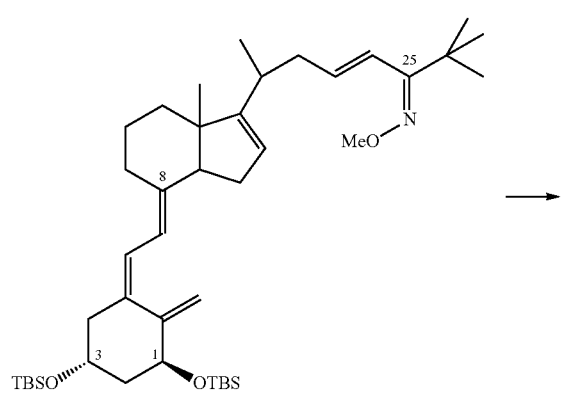

→

A 10 mL recovery flask was charged with this oil dissolved in 1.0 mL distilled THF, and to this solution was added tetra-n-butylammonium fluoride (28 μL of a 1M solution in THF, 0.028 mmol) via syringe at room temperature. The mixture was allowed to stir at room temperature in the dark for 24 hours, at which point, TLC showed the completion of the reaction. This mixture was directly purified by a column chromatography (99% ethyl acetate buffered with 1% triethylamine) to give 4.3 mg (81%, 39% overall) of I(e). This analog was further purified by HPLC (Semipreparative (1×25 cm) Chiracel OD, 2.5 mL/min) (3-10% isopropyl alcohol/hexanes) to give 3.4 mg (67%, 32% overall yield). (The trace injection of this HPLC purified material with the same assay showed that I(e) is greater than 99.9% pure). The retention time of I(e) is 11.6 minutes. $[\alpha]^{25}_D$=−7.3 (c 0.14, CHCl₃); ¹H NMR (CDCl₃, 400 MHz): δ 6.38 (d, 1H, J=11.2 Hz), 6.34-6.26 (m, 1H), 6.11 (d, 1H, J=11.6 Hz), 5.90 (d, 1H, J=16.0 Hz), 5.34-5.33 (m, 2H), 5.01-5.00 (m, 1H), 4.45 (br, 1H), 4.24 ((br, 1H), 3.82 (s, 3H), 2.81 (dd, 1H, J=4.8, 12.4 Hz), 2.60 (dd, 1H, J=5.0 Hz, J=10.4 Hz), 2.43-2.17 (m, 7H), 2.07-1.88 (m, 3H), 1.80-1.66 (m, 4H), 1.14 (s, 9H), 1.05 (d, 3H, J=6.8 Hz), 0.70 (s, 3H); ¹³C NMR (CDCl₃, 100 MHz): δ 160.6, 159.1, 147.6, 142.5, 139.9, 132.9, 124.9, 121.0, 119.9, 116.9, 111.7, 70.7, 66.9, 61.5, 58.4, 50.1, 45.1, 42.8, 41.1, 36.9, 35.3, 32.7, 29.4, 28.7, 28.1, 23.6, 21.1, 16.9; IR (Thin Film) 3377 (m), 2954 (s), 2919 (m), 1454 (m), 1366 (w), 1202 (w), 1049 (s), 967 (w), 884 (w) cm⁻¹; HRMS: calcd for $C_{30}H_{45}NO_3Na^+$ [M+Na]: 490.3291. found: 490.3308; UV (MeOH) $\lambda_{max}$ 240 nm (ε 12,274). 100 μg samples were prepared by dissolving 3.4 mg of analog in 3.4 mL ACS grade methyl alcohol and distributing it into vials as 100 μL solutions. Then, the each vial was concentrated in vacuo. The UV spectrum was taken by using one of the 100 μg samples of I(e) that was dissolved in 3 mL ACS grade methyl alcohol.

Example 4

CYP24 Enzyme Assay (i) Material and Reagents:
³H-1a,25(OH)₂D₃
Substrates (1 mM) reconstituted in isopropanol
V79-CYP24 cells
DMEM media supplemented with hygromycin and 5% fetal bovine serum
DMEM+1% BSA media
DPPD
96-well plate methanol
dichlorimethane
saturated KCl: KCl 30 g, $H_2O$ 00 ml
ketoconazole
(ii) Procedure:
1. Preparation of Cell Suspension
On the day of the assay, washed the monolayer of V79-CYP24 cells once with 1×PBS buffer and then trypsinized for 5 min at room temperature (approx. 22° C.). Added 1×PBS. Collected cells into tube, centrifuged cells (500×g, 5 min) and resuspended in DMEM+1% BSA media. Counted cells and adjusted density to 2 million/1 mL.
2. Cell Plating
Added 80 μl of cell suspension to appropriately labeled wells of a 96-well plate. Incubated plate for 45 minutes at 37° C. in a humidified atmosphere containing 5% $CO_2$.
3. Compound Addition
Added 10 μl of inhibitor ($10^{-6}$ to $10^{-10}$ M) and then after 35-40 min added 10 μl of substrate [$^3$H-1β]-1α,25(OH)$_2$D$_3$ (20 nM) for 2 hours at 37° C. in a humidified atmosphere containing 5% $CO_2$. Both inhibitor and substrate were prepared in DMEM with 1% BSA media.
4. Lipid Extraction and Counting
Added 250 μl of methanol to stop the reaction and mixed. Added 125 ml of dichloromethane, covered block and vortexed. Added 125 ml of dichloromethane again, added 125 ml of saturated KCl and vortexed. Centrifuged at 3000 rpm for 30 min. Triplicate 100 μl aliquots of aqueous fraction were mixed with 200 μl of scintillation fluid and the radioactivity was measured using a scintillation counter. All values were normalized for background.
(iii) Results:
1. Compound (20R)-I(a) had an $IC_{50}$ of 487.5 nM in the inhibition of CYP24 in this assay.
2. Compound (20R)-I(c) had an $IC_{50}$ of 85.9 nM in the inhibition of CYP24 in this assay.
3. Compound (20R)-I(e) had an $IC_{50}$ of 20.7 nM in the inhibition of CYP24 in this assay.
(iv) Reference:
1. PCT Patent Application Serial No. PCT/CA03/00620

Example 5

CYP27A1 Enzyme Assay (A) Procedure:
As described in:
Dilworth F J, Black S M, Guo Y D, Miller W L, Jones G. Construction of a P450c27 fusion enzyme: a useful tool for analysis of vitamin D$_3$ 25-hydroxylase (1996) Biochem J 320:267-271
Sawada N, Sakaki T, Ohta M, Inouye K. Metabolism of vitamin D (3) by human CYP27A1 (2000) Biochem Biophys Res Commun 273(3):977-84
(B) Results:
Compounds (20R)-I(e) had an $IC_{50}$ greater than 1000 nM in the inhibition of CYP27A1 in this assay.

Example 6

VDR Binding Assay (i) Reagent and Materials:
1. VDR 9.4 μmol/μl (human, recombinant, Biomol).
2. [$^3$H]-1,25(OH)$_2$D$_3$ in ethanol
3. 1,25(OH)$_2$D$_3$ in ethanol
4. TEK$_{300}$
Tris-HCl 50 mM
EDTA 1.5 mM
KCl 300 mM
Adjusted pH to 7.4 (25° C.)
5. TEDK$_{300}$
TEK$_{300}$
DTT (dithiothreitol) 10 mM (MW 154.24)
6. Tris buffer
22.50 g Tris-HCl
500 ml $H_2O$
13.25 g Tris-base
500 ml $H_2O$
Kept in 4° C.
7. Dextran-T70 (Mol 70,000) Pharmacia
8. Charcoal (carbon decolorizing neutral, norit) Fisher Scientific
9. Gelatin (G-2625 Sigma)
(ii) Reagent Preparation:
1. Charcoal Dextran Solution
(1) Tris Buffer
Mixed equal amount of Tris-HCl and Tris-base.
(2) Norit decolorizing neutral charcoal 2.0 g
Tris buffer 150 mL
Stirred
(3) Dextran T-70 0.2 g
Tris buffer 50 ml.
(4) Slowly dripped the suspended dextran into charcoal solution with stirring.
Kept in refrigerator overnight.
Thirty minutes before use, stored on ice with continuous mixing.
2. TEK$_{300}$/Gelatin solution
50 mg swine gelatin
5 ml TEDK$_{300}$ solution
heated, stirred then cooled to 4° C.
5 ml TEDK$_{300}$ solution
3. Preparation of 1,25(OH)$_2$D$_3$ and test compounds in ethanol:
1,25(OH)$_2$D$_3$: 125, 250, 500, 1000, 2000, 4000 pg/25 μl. (stock 10-5 M/25 μL=100,000 pg/25 μL)

| Concentration (ng/mL) | Amount (pg/50 μL) |
| --- | --- |
| 5.0 | 125 |
| 10.0 | 250 |
| 20.0 | 500 |
| 40.0 | 1000 |
| 80.0 | 2000 |
| 160.0 | 4000 |

Test compounds: 12,500, 25,000, 50,000, 100,000, 200,000 and 400,000 pg/25 μL. (4*10-5M/25 μL=400,000 pg/25 L)
4. Dilution of VDR:
1 μl stock VDR in 2.5 ml TEDK$_{300}$/Gelatin solution (500 μl/tube), (kept on ice)
(iii) Procedure:
1. Reaction Setup
Labeled tubes according to the following chart, each in triplicate:

| No VDR Control | No VD3 Control | Standard | Test Compounds |
|---|---|---|---|
| Added 25 μL ethanol | Added 25 μL ethanol | Added 25 μL of each standard (in each concentration) | Added 25 μL of each sample (in each concentration) |
| Added 500 μL TEDK300/gelatin solution | Added 500 μL VDR working solution | Added 500 μL VDR working solution | Added 500 μL VDR working solution |

Mixed all tubes via vortex and incubated at room temperature for 1 hour. Added 10 μL of 3H-1,25(OH)$_2$D$_3$ Working Dilution, mixed by vortex and incubated at room temperature for 1 hour.

2. Sample Processing

Thirty minutes before addition, put Charcoal/Dextran Solution on ice with continuous mixing. Added 100 μL of Charcoal/Dextran Solution to each tube, mixed well and incubated on ice for 30 minutes. Centrifuged @ 2000 rpm for 10 minutes at 4° C.

3. Counting

Pipetted 100 μL of the upper, aqueous phase to a 24 well scintillation counting plate and added 600 μL scintillation fluid per well, covered and mixed well. Counted the plate using a scintillation counter for 5 min/sample.

(iv) Calculations:

The amount of 1,25(OH)$_2$D$_3$ to displace 50 percent [$^3$H]-1,25(OH)$_2$D$_3$ from VDR was calculated as B$_{50}$ for 1,25(OH)$_2$D$_3$. The VDR binding of other compounds was calculated as B$_{50}$ relative to a value of 1 for 1,25(OH)$_2$D$_3$.

Serial Dilution of 1,25(OH)D$_3$

| Concentration (pg/25 μl) | Final concentration M | $10^{-5}$ M (μl) | Ethanol (μl) |
|---|---|---|---|
| 4,000 | $2 \times 10^{-8}$ | 6 | 144 |
| 2,000 | $10^{-8}$ | 70 | 70 |
| 1,000 | $5 \times 10^{-9}$ | 70 | 70 |
| 500 | $2.5 \times 10^{-9}$ | 70 | 70 |
| 250 | $1.25 \times 10^{-9}$ | 70 | 70 |
| 125 | $6.25 \times 10^{-10}$ | 70 | 70 |

Serial Dilution of Test Compounds

| Concentration (pg/50 μl) | Final concentration M | $10^{-3}$ M (μl) | Ethanol (μl) |
|---|---|---|---|
| 400,000 | $2 \times 10^{-6}$ | 6 | 144 |
| 200,000 | $10^{-6}$ | 70 | 70 |
| 10,000 | $5 \times 10^{-7}$ | 70 | 70 |
| 5,000 | $2.5 \times 10^{-7}$ | 70 | 70 |
| 25,000 | $1.25 \times 10^{-7}$ | 70 | 70 |
| 12,500 | $6.25 \times 10^{-8}$ | 70 | 70 |

(v) Results:

Compound of Formula (20R)-I(e) had a B$_{50}$ of 60 nM.

(vi) References:
1. Ross T K, Prahl J M, DeLuca H. Overproduction of rat 1,25-dihydroxy vitamin D$_3$ receptor in insect cells using the baculovirus expression system. (1991) Proc Natl Acd Sci USA 88:6555-6559
2. Wecksler W R, Norman A W. An hydroxapatite batch assay for the quantitation of 1alpha, 25-dihydroxy vitamin D$_3$-receptor complexes (1979) Anal Biochem 92:314-323

Example 7

DBP Binding Assay

Human Plasma (A) Reagents:
1. Tris buffer:
22.50 g Tris-HCl
500 ml H$_2$O
2. 13.25 g Tris-base
500 ml H$_2$O
Kept in 4° C.
3. Dextran-T70 (Mol 70,000) Pharmacia
4. Charcoal (carbon decolorizing neutral, norit) Fishery
5. DBP (vitamin D binding protein) (human plasma)
6. [$^3$H] 25(OH)D$_3$
7. Gelatin (G-2625 Sigma)

(B) Reagent Preparation:
1. Tris buffer
Mixed equal volume of two Tris buffer.
2. Dextran Coated Charcoal Solution
(1) preparation of charcoal solution
Norit decolorizing neutral charcoal 2.0 g
Tris buffer 150 mL
Stirring
(2) preparation of dextran solution
Dextran T—70 0.2 g
Tris buffer 50 ml
(3) preparation of dextran coated charcoal solution
Slowly dripped the dextran solution into charcoal solution with stirring.
Kept refrigerated overnight.
Thirty minute before use, kept it on ice with continuous mixing.
This solution can be kept in 4° C. for 2 month.
3. Tris Buffer/Gelatin Solution
250 mg swine gelatin
50 ml Tris buffer
heating, stirring and cooling on ice.
Prepared just before use.
4. DBP Solution
Human plasma diluted to 1:5000 with Tris buffer/gelatin solution
5. Dilution of Standard 25(OH)D$_3$
Stock 10,000 pg/50 μl
Diluted to 0, 62.5, 125, 250, 500, 750, 1000, 10,000 pg/50 μl with ethanol
6. Dilution of Standard 1,25(OH)$_2$D$_3$
Stock 200,000 pg/50 μl ($10^{-5}$ M/50 μl)
Diluted to 6,250, 12,500, 25,000, 50,000, 100,000, 200,000 pg/50 μl with ethanol
7. Dilution of Test Compounds
Stock 200,000 pg/50 μl ($10^{-3}$ M)
Diluted to 12,500, 25,000, 50,000, 100,000, 200,000 and 400,000 pg/50 μl with ethanol
8. [$^3$H-26,27]-25(OH)$_2$D$_3$ Solution
Stock solution diluted in Tris buffer, 20,000 CPM/50 μl.

(C) Assay

| Label | 25(OH)D$_3$ | Test compound (μl) | 3H—25(OH)D$_3$ (μl) | DBF (μl) | Supermix | Incubation (Rm T) | Charcoal dextran (μl) | On ice | Centrifuge | Counting |
|---|---|---|---|---|---|---|---|---|---|---|
| 1-3 (total) | — | — | 50 | — | 600 | — | — | — | — | — |
| 4-8 | — | — | 50 | 500 | 600 | — | — | — | — | — |
| STD 5-35 | 50 | — | 50 | — | — | 4 h | 200 | 1 h | 2000 rpm 15 min, 4° C. | 200 μl Super + 600 μl Supermix |
| Test 36- | — | 50 | 50 | — | — | | | | | |

(D) Calculation:

The amount of 25(OH)D$_3$ to displace 50 percent [3H]-25(OH)D$_3$ was calculated as B$_{50}$ for 25(OH)D$_3$ DBP binding. The DBP binding of other compounds was calculated as B$_{50}$ relative to a value of 1 for 25(OH)D$_3$.

(E) Dilution of 25(OH)D$_3$:

| Amount (mol/50 μl) | From previous steps (μl) | Ethanol (μl) |
|---|---|---|
| 2.5*10$^{-11}$ (5*10$^{-7}$ M) | 5*10$^{-7}$ M | |
| 2.5*10$^{-12}$ | 40 | 360 |
| 1.875*10$^{-12}$ | 90 | 30 |
| 1.25*10$^{-12}$ | 130 | 130 |
| 6.25*10$^{-13}$ | 130 | 130 |
| 3.125*10$^{-13}$ | 130 | 130 |
| 1.5625*10$^{-13}$ | 130 | 130 |

(F) Dilution of 1,25(OH)D$_3$:

| Amount (mol in 50 μl) | From previous steps (μl) | Ethanol (μl) |
|---|---|---|
| 5*10$^{-10}$ (10$^{-5}$ M) | | |
| 2.5*10$^{-10}$ | 130 | 130 |
| 1.25*10$^{-10}$ | 130 | 130 |
| 6.25*10$^{-11}$ | 130 | 130 |
| 3.215*10$^{-11}$ | 130 | 130 |
| 1.625*10$^{-11}$ | 130 | 130 |

(G) Dilution of Test Compounds:

| Amount (mol in 50 μl) | From previous steps (μl) | Ethanol (μl) |
|---|---|---|
| Stock (10$^{-3}$ M) | | |
| 1.0*10$^{-9}$ | 5 | 245 |
| 5.0*10$^{-10}$ | 130 | 130 |
| 2.5*10$^{-10}$ | 130 | 130 |
| 1.25*10$^{-10}$ | 130 | 130 |
| 6.25*10$^{-11}$ | 130 | 130 |
| 3.125*10$^{-11}$ | 130 | 130 |

(H) Results: The compound of Formula (20R)-I(e) showed a B$_{50}$ in this assay of >3500 nM.

(I) References: Bouillon R, van Baelen H, Moor P D. Comparative study of the affinity of the serum vitamin D-binding protein. (1980) J Steroid Biochem 13:1029-44.

Jones L, Byrnes B, Palma F, Segev D, Mazur E. Displacement potency of vitamin D$_2$ analogue in competitive protein-binding assay for 25-hydroxyvitamin D$_3$, 24,25-dihydroxyvitamin D$_3$ and 1,25-dihydroxyvitamin D$_3$ (1980) J Clin Endocrinol Metab 50:773-775

Example 8

CYP24 Transcriptional Activation Assay (i) Material and Reagents:
1α,25(OH)$_2$D$_3$ 1 mM reconstituted in isopropanol
Compound (1 mM) reconstituted in isopropanol
U-937 cells
RPMI media supplemented with:
  Sodium pyruvate
  Non-essential amino acids
  HEPES
  10% fetal bovine serum
Phorbol 12-myristate 13-acetate (PMA)
24-well plate
Isopropanol
TRIzol® reagent (Invitrogen)
Chloroform
Ethanol
Diethylpyrocarbonate treated dH$_2$O
Thermoscript™ RT-PCR System kit (Invitrogen)
Human CYP24 TaqMan® Probe (Applied Biosystems Inc)
Human GAPDH TaqMan® Probe (Applied Biosystems Inc)
TaqMan® Universal Master Mix Probe (Applied Biosystems Inc)

(ii) Procedure:
1. Cell Culture, Stimulation and Plating
  Cultured U-937 cells in 4+RPMI media to a level of ≈80% confluence. Pelleted cells by centrifugation and resuspended to a concentration of 5×10$^5$ cells per 1 ml media. Treated U-937 cells with a final concentration of PMA of 20 ng/ml. To each well, of a 24-well plate, added 1 ml of cell suspension and incubated overnight at 37° C., in a humidified atmosphere containing 5% CO$_2$, for adherence of cells to the wells.

2. Cell Treatment and TRIzol® Addition
  Changed the media with 1 ml of fresh 4+RPMI media. Added 1 μl of the working solutions of 1, 10, and 100 μM of the compound being tested, in triplicate. Added 1 μl of isopropanol as a control, in triplicate. Incubated the cells for six hours at 37° C., in a humidified atmosphere containing 5% CO$_2$, aspirated off the media and then added 1 ml of TRIzol® reagent. Transferred TRIzol® with cell lysate to a 1.7 ml microcentrifuge tube and stored at −80° C.

3. RNA Isolation and cDNA Synthesis
  Isolated total RNA from the 1 ml of TRIzol® through phase separation, RNA precipitation, and RNA washed as per manufacturer's instructions (Invitrogen). Determined the concentration of RNA using a spectrophotometer to measure the optical density of each sample, at a wavelength of 260 nm. Synthesized cDNA from 1 μg of RNA using the ThermoScript™ RT-PCR System kit as per manufacturer's instructions (Invitrogen). Added an additional 180 μl of dH$_2$O to each sample and stored at −20° C.

4. CYP24/GAPDH Real Time PCR

Determined the amount of CYP24 and GAPDH mRNA present in each sample using commercial TaqMan® probes, from Applied Biosystems Inc. (Foster City, Calif.). Detected both genes in the same 20 μl reaction, using an ABI PRISM 96-well optical reaction plate and cycle 50 times using an ABI Prism 7000 Sequence Detection System® (ABI). Used the Comparative $C_T$ method (ABI) to calculate the relative fold induction of each sample. Normalized the expression of CYP24 to the expression of the endogenous control, GAPDH, and compared the level of induction of each sample to 100 nM calcitriol set to 100%.

(iii) Results:

(i) The compound of Formula (20R)-I(a) showed an activity that was 54% of that for calcitriol at 100 nM.
(ii) The compound of Formula (20R)-I(c) showed an activity that was 30% of that for calcitriol at 100 nM. (iii) The compound of Formula (20R)-I(e) showed an activity that was 65% of that for calcitriol at 100 nM.

Example 9

[$^3$H]-Thymidine Proliferation Assay with MCF-7 Cells (i) Materials and Methods:
MCF-7 cells
MEM supplemented with sodium pyruvate, non-essential amino acids, bovine insulin, gentamycin and 10% Fetal bovine serum (growth media)
RPMI1640 supplemented with tri-iodothyronine, hydrocortisone, transferin, bovine insulin and 5% Fetal bovine serum (proliferation media)
Compound (1 mM) reconstituted in isopropanol
Trypsin:EDTA solution
1×PBS
75 cm$^2$ tissue culture flasks
96 well tissue culture plates
Liquid scintillation fluid
96 well filter plate (Millipore)
(ii) Procedure:
  1. Preparation of Cell Suspension.
    When MCF-7 cells were 70-80% confluent, aspirated growth media. Washed the cells with 1×PBS. Trypsinized with trypsin-EDTA from the plate, collected cells from the tissue culture flask, centrifuged (500×g, 5 min) and resuspended in growth media.
  2. Cell Plating.
    Counted the cells and adjusted the cell density to 25,000/ml. Added 200 μl per well in a 96 well plate. Incubated plate for 24 h at 37° C. in a humidified atmosphere plus 5% CO$_2$. Aspirated used media and replaced with 175 μl per well with proliferation media.
  3. Substrate Addition.
    Added 25 μl of compound (final concentration 10$^{-7}$ M, 5×10$^{-8}$ M, 10$^{-8}$ M, 5×10$^{-9}$ M, 10$^{-10}$ M or 0 M) into each designated well. Incubated plates for 3 days at 37° C. in a humidified atmosphere plus 5% CO$_2$.
  4. $^3$H-Thymidine Incorporation.
    Added $^3$H-thymidine at 0.02 μCi per well and incubated at 37° C. in a humidified atmosphere plus 5% CO$_2$ for 6 h.
  5. Plate Harvesting.
    Aspirated all media and washed cells with 1×PBS. Trypsinized cells for 30 min at 37° C. in a humidified atmosphere plus 5% CO$_2$. Harvested cells onto a 96 well filter plate (Millipore) using a Tomtec Cell Harvestor, according to manufacturers instructions.
  6. Scintillation Counting.
    Added 25 μl of scintillation fluid per well. Counted the plate using a scintillation counter.
Results: Compound (20R)-I(e) inhibited MCF-7 cell proliferation.

Example 10

[$^3$H]-Thymidine Proliferation Assay with SCC-25 Cells (i) Materials and Methods:
SCC-25 cells
DMEM-F12 supplemented with hydrocortisone and 5% Fetal bovine serum
1α,25(OH)$_2$D$_3$ 1 mM reconstituted in isopropanol
Substrates (1 mM) reconstituted in isopropanol
Trypsin:EDTA solution
1×PBS
75 cm$^2$ tissue culture flasks
96 well tissue culture plates
Liquid scintillation fluid
96 well filter plate (Millipore)
(ii) Procedure:
  1. Preparation of Cell Suspension
    When SCC-25 cells were 70-80% confluent, aspirated media. Washed the cells with 1×PBS. Trypsinized with trypsin-EDTA from the plate, collected cells from the tissue culture flask, centrifuged (500×g, 5 min) and resuspended in media.
  2. Cell Plating.
    Counted the cells and adjusted the cell density to 10,000/ml. Added 200 μl per well in a 96 well plate. Incubated plate for 24 h at 37° C. in a humidified atmosphere plus 5% CO$_2$. Aspirated used media and replaced with 175 μl per well with media.
  3. Substrate Addition.
    Added 25 μl of compound (final concentration 10$^{-7}$ M, 5×10$^{-8}$ M, 10$^{-8}$ M, 5×10$^{-9}$ M, 10$^{-10}$ M or 0 M) into each designated well. Incubated plates for 3 days at 37° C. in a humidified atmosphere plus 5% CO$_2$.
  4. $^3$H-Thymidine Incorporation.
    Added $^3$H-thymidine at 0.02 μCi per well and incubated at 37° C. in a humidified atmosphere plus 5% CO$_2$ for 6 h.
  5. Plate Harvesting.
    Aspirated all media and washed cells with 1×PBS. Trypsinized cells for 30 min at 37° C. in a humidified atmosphere plus 5% CO$_2$. Harvested cells onto a 96 well filter plate (Millipore) using a Tomtec Cell Harvestor, according to manufacturers instructions.
  6. Scintillation Counting.
    Added 25 μl of scintillation fluid per well. Counted the plate using a scintillation counter.
Results: Compound (20R)-1(e) inhibited SCC-25 cell proliferation.

Example 11

[³H]-Thymidine Proliferation Assay with LNCaP Cells (i) Materials and Methods:
LNCaP cells
RPMI 1640 medium with 2 mM L-glutamine adjusted to contain 1.5 g/L sodium bicarbonate, 4.5 g/L glucose, 10 mM HEPES, and 1.0 mM sodium pyruvate, 90%; fetal bovine serum, 10%
1α,25(OH)$_2$D$_3$ 1 mM reconstituted in isopropanol
Substrates (1 mM) reconstituted in isopropanol
Trypsin:EDTA solution
75 cm² tissue culture flasks
96 well tissue culture plates
Liquid scintillation fluid
96 well filter plate (Millipore)
(ii) Procedure:
1. Preparation of Cell Suspension.
   When LNCaP cells were 70-80% confluent, aspirated media. Washed the cells with 1×PBS. Trypsinized with trypsin-EDTA from the plate, collected cells from the tissue culture flask, centrifuged (500×g, 5 min) and resuspended in media.
2. Cell Plating.
   Counted the cells and adjusted the cell density to 2,000/ml. Added 200 µl per well in a 96 well plate. Incubated plate for 24 h at 37° C. in a humidified atmosphere plus 5% CO$_2$. Aspirated used media and replace with 175 µl per well with media.
3. Substrate Addition.
   Added 25 µl of compound (final concentration $10^{-7}$ M, $5 \times 10^{-8}$ M, $10^{-8}$ M, $5 \times 10^{-9}$ M, $10^{-10}$ M or 0 M) into each designated well. Incubated plates for 3 days at 37° C. in a humidified atmosphere plus 5% CO$_2$.
4. ³H-Thymidine Incorporation.
   Added ³H-thymidine at 0.02 µCi per well and incubated at 37° C. in a humidified atmosphere plus 5% CO$_2$ for 6 h.
5. Plate Harvesting.
   Aspirated all media. Trypsinized cells for 30 min at 37° C. in a humidified atmosphere plus 5% CO$_2$. Harvested cells onto a 96 well filter plate (Millipore) using a Tomtec Cell Harvestor, according to manufacturers instructions.
6. Scintillation Counting.
   Added 25 µl of scintillation fluid per well. Counted the plate using a scintillation counter.

Results: Compound (20R)-I(e) inhibited LNCaP cell proliferation.

Example 12

[³H]-Thymidine Proliferation Assay with BxPC-3 Cells (i) Materials and Methods:
BxPC-3 cells
RPMI 1640 medium with 2 mM L-glutamine adjusted to contain 1.5 g/L sodium bicarbonate, 4.5 g/L glucose, 10 mM HEPES, and 1.0 mM sodium pyruvate, 90%; fetal bovine serum, 10%
1α,25(OH)$_2$D$_3$ 1 mM reconstituted in isopropanol
Substrates (1 mM) reconstituted in isopropanol
Trypsin:EDTA solution
1×PBS
75 cm² tissue culture flasks
96 well tissue culture plates
Liquid scintillation fluid
96 well filter plate (Millipore)
(ii) Procedure:
1. Preparation of Cell Suspension
   When BxPC-3 cells were 70-80% confluent, aspirated media. Washed the cells with 1×PBS. Trypsinized with trypsin-EDTA from the plate, collected cells from the tissue culture flask, centrifuged (500×g, 5 min) and resuspended in media.
2. Cell Plating.
   Counted the cells and adjusted the cell density to 2,000/ml. Added 200 µl per well in a 96 well plate. Incubated plate for 24 h at 37° C. in a humidified atmosphere plus 5% CO$_2$. Aspirated used media and replaced with 175 µl per well with media.
3. Substrate Addition.
   Added 25 µl of compound (final concentration $10^{-7}$ M, $5 \times 10^{-8}$ M, $10^{-8}$ M, $5 \times 10^{-9}$ M, $10^{-10}$ M or 0 M) into each designated well. Incubated plates for 3 days at 37° C. in a humidified atmosphere plus 5% CO$_2$.
4. ³H-Thymidine Incorporation.
   Added ³H-thymidine at 0.02 µCi per well and incubated at 37° C. in a humidified atmosphere plus 5% CO$_2$ for 6 h.
5. Plate Harvesting.
   Aspirated all media and washed cells with 1×PBS. Trypsinized cells for 30 min at 37° C. in a humidified atmosphere plus 5% CO$_2$. Harvested cells onto a 96 well filter plate (Millipore) using a Tomtec Cell Harvestor, according to manufacturers instructions.
6. Scintillation Counting.
   Added 25 µl of scintillation fluid per well. Counted the plate using a scintillation counter.

Results: Compound (20R)-I(e) inhibited BxPC-3 cell proliferation.

Example 13

[³H]-Thymidine Proliferation Assay with OVCAR-3 Cells (i) Materials and Methods:
OVCAR-3 cells
RPMI 1640 medium with 2 mM L-glutamine supplemented with 10 mM HEPES, 1.0 mM sodium pyruvate, 0.01 mg/ml bovine insulin and 10% fetal bovine serum
1α,25 (OH)$_2$D$_3$ 1 mM reconstituted in isopropanol
Substrates (1 mM) reconstituted in isopropanol
Trypsin:EDTA solution
1×PBS
75 cm2 tissue culture flasks
96 well tissue culture plates
Liquid scintillation fluid
96 well filter plates (Millipore)
(ii) Procedure:
1. Preparation of Suspension
   When OVCAR-3 cells were ~50% confluent, aspirated media. Washed cells with 1×PBS. Trypsinized with trypsin-EDTA, collected cells from the tissue culture flask, centrifuged (200×g, 5 min) and resuspended in media.
2. Cell Plating.
   Counted the cells and adjusted the cell density to $11.4 \times 10^3$ to provide 2000 cells in 175 µl (for 1 well). Distributed cell suspension into a 96 well plates at 175 µl (2000 cells) per well. Incubated plate for 24 h at 37° C. in a humidified atmosphere plus 5% CO$_2$.

Substrate addition.

Added 25 μl of compound (final concentration $10^{-7}$ M, $5 \times 10^{-8}$ M $10^{-8}$ M, $5 \times 10^{-9}$ M, $10^{-9}$ M, $10^{-10}$M or 0 M) into each designated well. Incubated plates for 6 days without changing media and drugs at 37° C. in a humidified atmosphere plus 5% $CO_2$.

3. [$^3$H]-Thymidine incorporation

Added $^3$H-thymidine at 0.02 μCi per well and incubated at 37° C. in a humidified atmosphere plus 5% $CO_2$ for 6 h.

4. Plate Harvesting.

Aspirated all media and washed cells with 1×PBS. Trypsinized cells for 30 min at 37° C. in a humidified atmosphere plus 5% $CO_2$. Harvested cells onto a 96 well filter plate (Millipore) using a Tomtec Cell Harvestor, according to manufacturers instructions.

5. Scintillation Counting.

Added 25 μl of scintillation fluid per well. Counted the plate using a scintillation counter.

Results: Compounds (20R)-I(a), (20R)-I(c) and (20R)-I(e) all inhibited the proliferation of OVCAR-3 cells.

Example 14

Pharmacokinetics of Compound (20R)-I(e)

(i) Materials and Reagents:

A formulation of compound (20R)-I(e) dissolved in saline (0.9% NaCl): propylene glycol:ethanol (5:3:2; v/v/v) was prepared at a concentration of 20 mg/ml.

(ii) Procedure:

Nine male Wistar rats (150-200 g) were fasted 8 hours prior to the initiation of the study. At the initiation of the study, the nine rats received 0.8 ml/kg body weight (B.W.) of the dosing formulation by intravenous (i.v.) injection to deliver 16 mg of compound (20R)-I(e)/kg B.W. Blood was collected from three animals at 0 (day-1), 5, 15, 30, 60, 120, 180 and 240 minutes post dosing. At each time point, 1 ml of blood was collected from the orbital sinus in unpreserved Microtainer tubes. Separated serum samples were kept frozen at –80° C. until analysis.

The concentration of compound (20R)-I(e) in the serum samples was quantified using a High Performance Liquid Chromatographic method with Mass Spectroscopy detection (LC MS/MS). An internal standard was added to an aliquot of 200 ml of serum sample and extracted using solid phase extraction (SPE). Samples were passed through $C_{18}$-SPE cartridges then compound (20R)-I(e) and the internal standard were eluted with 1 ml of methanol. Extracts were evaporated to dryness under nitrogen. The residues were reconstituted in 100 ml of methanol:water (8:2; v/v) and analyzed by LC MS/MS.

(iii) Results:

Summary of the calculated pharmacokinetic parameters for the i.v. administration of a 16 mg/kg B.W. dose of compound (20R)-I(e) is in the Table below. The Area-Under-Curve (AUC) was calculated from T=0 to 240 min. The maximum concentration ($C_{max}$) was determined from the mean serum concentration versus time profile. The elimination half life ($T_{1/2}$) was calculated from the elimination phase of the concentration versus time profile assuming first order kinetic elimination.

| AUC (ng/ml × hr) | $T_{1/2}$ (hr) | $C_{max}$ (ng/ml) |
|---|---|---|
| 39.6 | 0.25 | 38.9 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

We claim:

1. A compound selected from a compound of Formula 1, and pharmaceutically acceptable salts thereof:

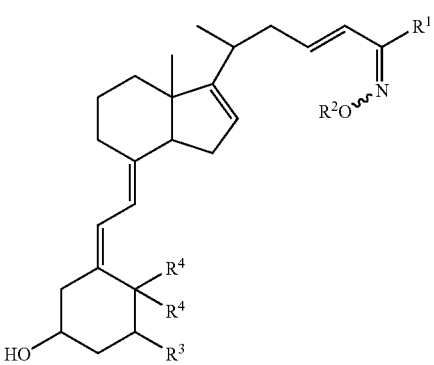

wherein
  $R^1$ is selected from the group consisting of $C_{1-6}$alkyl, $C_{2-6}$alkenyl, cyclo($C_3$-$C_6$)alkyl and cyclo($C_3$-$C_6$)alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, $NH_2$, $NHC_{1-4}$alkyl and $N(C_{1-4}$alkyl)($C_{1-4}$alkyl), and with cyclo($C_3$-$C_6$)alkyl and cyclo($C_3$-$C_6$)alkenyl being unsubstituted or substituted with 1-5 groups independently selected from $C_{1-4}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)($C_{1-4}$alkyl), CN, C(O)OH, C(O)O$C_{1-4}$alkyl, C(O)NH$C_{1-4}$alkyl, NHC(O)$C_{1-4}$alkyl, OC(O)$C_{1-4}$alkyl, SO$C_{1-4}$alkyl, $SO_2C_{1-4}$alkyl, $SO_2$NH$C_{1-4}$alkyl and $SO_2NH_2$;
  $R^2$ is selected from the group consisting of H, $C_{1-6}$alkyl and $C_{2-6}$alkenyl, with $C_{1-6}$alkyl and $C_{2-6}$alkenyl being unsubstituted or substituted with one or more halo groups or with 1-4 groups independently selected from $C_{1-4}$alkyl, $OC_{1-4}$alkyl, OH, halo, $NH_2$, $NHC_{1-4}$alkyl and $N(C_{1-4}$alkyl)($C_{1-4}$alkyl);
  $R^3$ is selected from the group consisting of OH, $OC_{1-6}$alkyl, and halo; and
  $R^4$ are either both H or together form $=CH_2$.

2. The compound according to claim 1, wherein R¹ is selected from the group consisting of CF₃, C(CF₃)₃, cyclopropyl and t-butyl.

3. The compound according to claim 2, wherein R¹ is t-butyl.

4. The compound according to claim 1, wherein R² is selected from the group consisting of CH₃, ethyl and allyl.

5. The compound according to claim 4, wherein R² is CH₃.

6. The compound according to claim 1, wherein R³ is selected from the group consisting of OH and fluoro.

7. The compound according to claim 6, wherein R³ is OH.

8. The compound according to claim 1, wherein R⁴ together form CH₂.

9. The compound according to claim 1, wherein the geometry about the C=N double bond of the oxime is trans.

10. The compound according to claim 1 having the following relative stereochemistry:

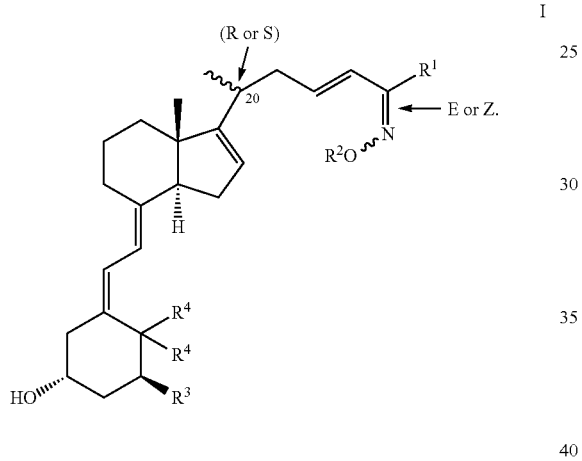

I

11. The compound according to claim 10, wherein the stereochemistry at C-20 is R.

12. The compound according to claim 1 that is selected from the group consisting of:

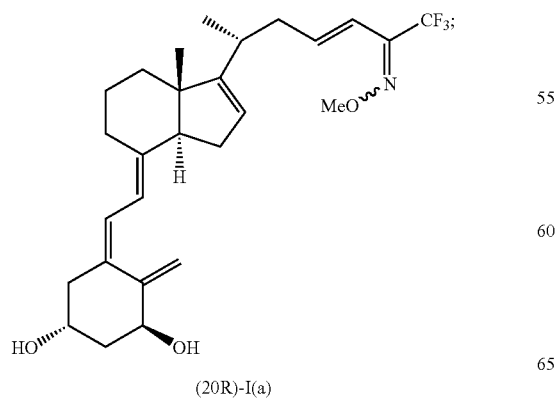

(20R)-I(a)

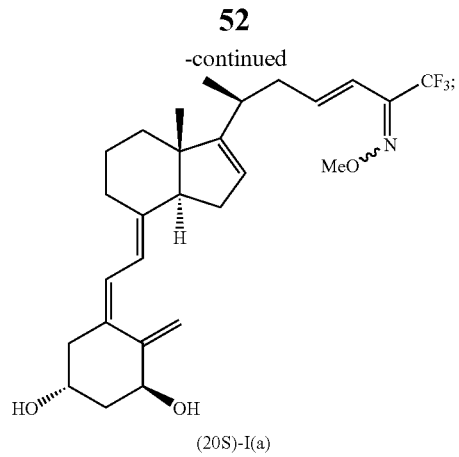

(20S)-I(a)

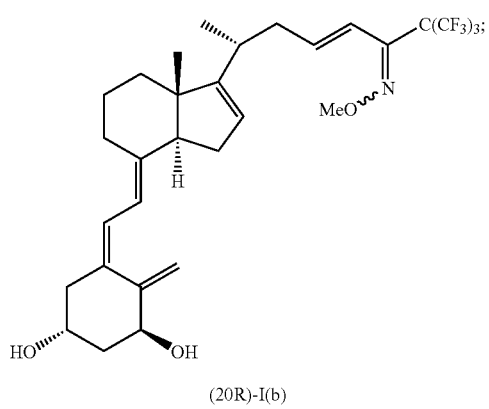

(20R)-I(b)

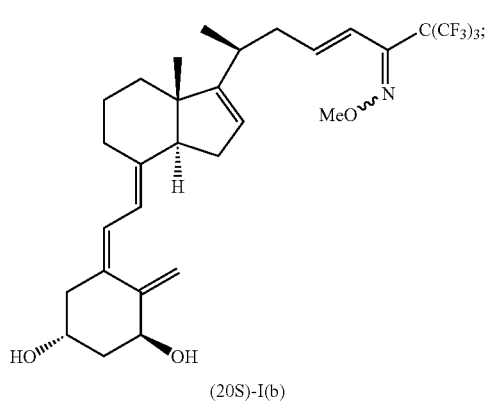

(20S)-I(b)

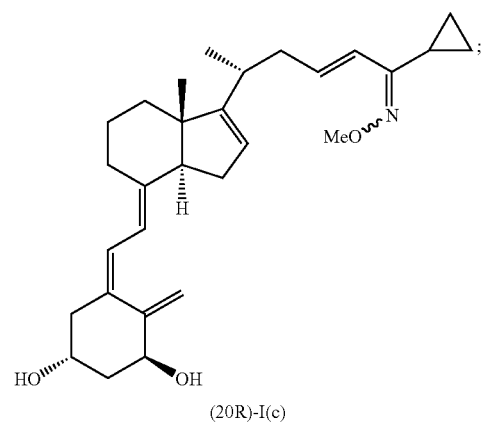

(20R)-I(c)

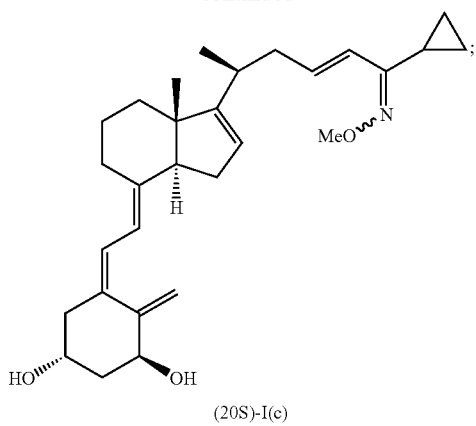
(20S)-I(c)
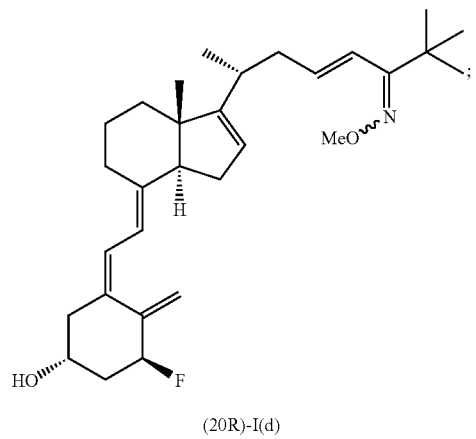
(20R)-I(d)
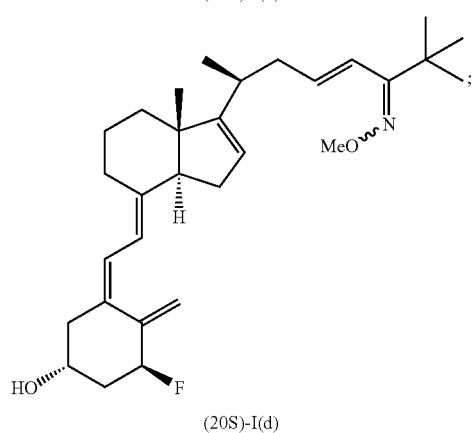
(20S)-I(d)
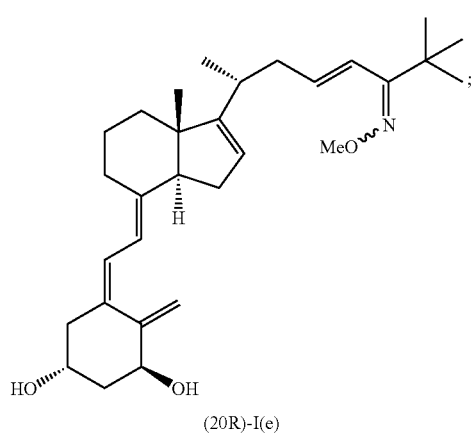
(20R)-I(e)
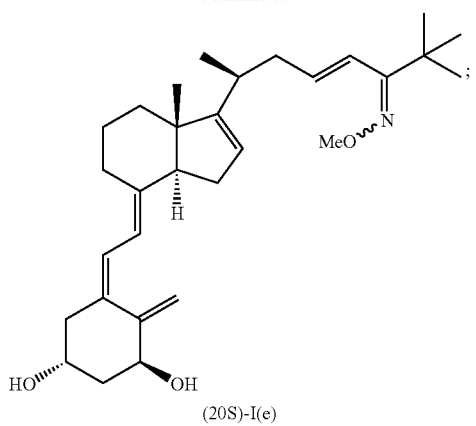
(20S)-I(e)
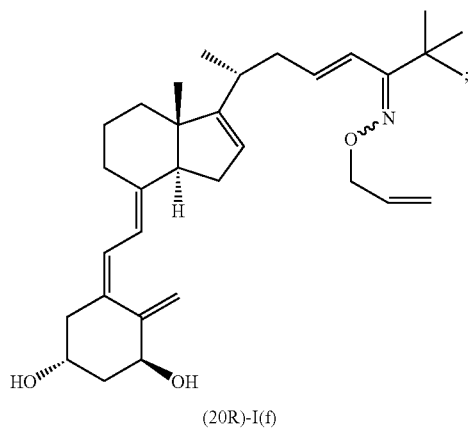
(20R)-I(f)
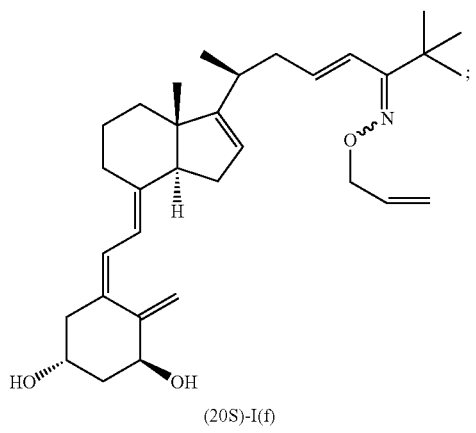
(20S)-I(f)
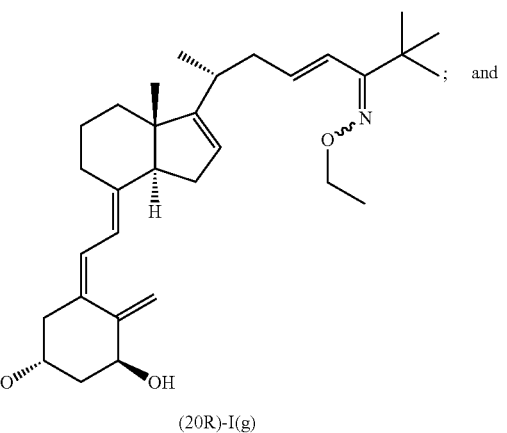
(20R)-I(g)

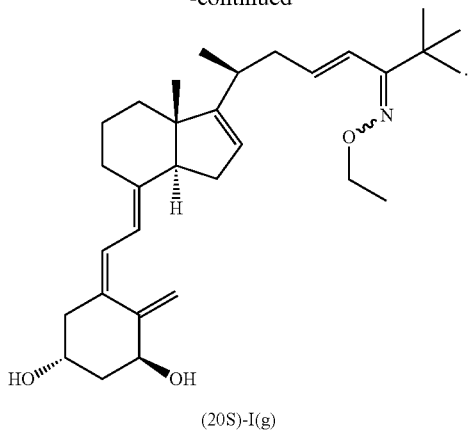

(20S)-I(g)

13. The compound according to claim 11, wherein the oxime double bond is in the E configuration.

14. A pharmaceutical composition comprising a compound as defined in claim 1 and a pharmaceutically acceptable carrier.

15. A method of treating a disease which benefits from an inhibition of the catabolism of 1α,25-dihydroxyvitamin $D_3$, wherein the disease is selected from the group consisting of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism, and osteoporosis, comprising administering an effective amount of a compound as defined in claim 1 to a cell or animal in need thereof.

16. The method according to claim 15, wherein the disease is selected from the group consisting of breast cancer, lung cancer, prostate cancer, colon cancer, colorectal cancer, kidney cancer, head and neck cancer, pancreatic cancer, Kaposi's sarcoma, leukemia.

17. A method for increasing the efficacy of a vitamin D receptor agonist which is a CYP24 substrate, comprising contemporaneously administering an effective amount of a compound according to claim 1 and an effective amount of the vitamin D receptor agonist to a cell or animal in need thereof.

18. The method according to claim 17, wherein the vitamin D receptor agonist is 1α,25-dihydroxyvitamin $D_3$.

19. The method according to claim 17, used to treat a disease selected from one or more of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis.

20. The method according to claim 19, wherein the disease is selected from the group consisting of breast cancer, lung cancer, prostate cancer, colon cancer, colorectal cancer, kidney cancer, head and neck cancer, pancreatic cancer, Kaposi's sarcoma, leukemia, psoriasis, hyperparathyroidism, secondary hyperparathyroidism and osteoporosis.

21. The method of claim 17, wherein the compound of claim 1 is

22. The compound, of claim 12 which is

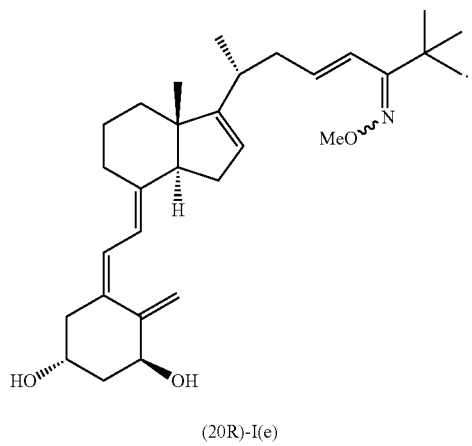 [SMILES: C=C1/C(=C\C=C2/CCC[C@]3(C)C([C@H](C)C/C=C/C(=NOC)C(C)(C)C)=CC[C@@H]23)C[C@@H](O)C[C@@H]1O]

(20R)-I(e)

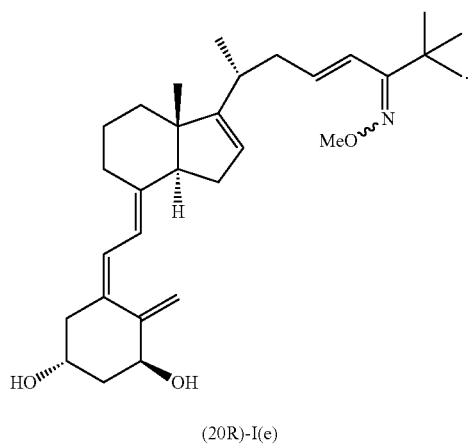 [SMILES: C=C1/C(=C\C=C2/CCC[C@]3(C)C([C@H](C)C/C=C/C(=NOC)C(C)(C)C)=CC[C@@H]23)C[C@@H](O)C[C@@H]1O]

(20R)-I(e)

23. The pharmaceutical composition of claim 14 wherein the compound of claim 1 is

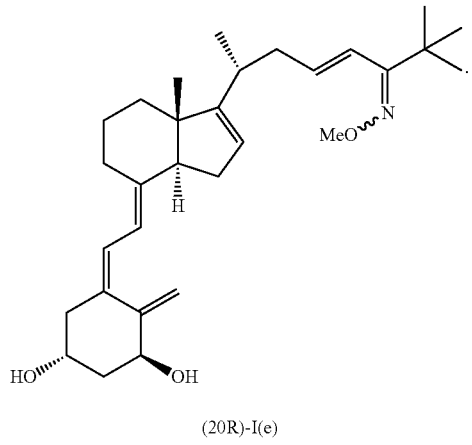 [SMILES: C=C1/C(=C\C=C2/CCC[C@]3(C)C([C@H](C)C/C=C/C(=NOC)C(C)(C)C)=CC[C@@H]23)C[C@@H](O)C[C@@H]1O]

(20R)-I(e)

* * * * *